(12) United States Patent
Allsop et al.

(10) Patent No.: US 7,221,814 B2
(45) Date of Patent: May 22, 2007

(54) OPTICAL WAVEGUIDE BASED SURFACE PROFILING APPARATUS

(75) Inventors: Thomas David Paul Allsop, Birmingham (GB); Timothy Earthrowl-Gould, Birmingham (GB); Ian Bennion, Birmingham (GB)

(73) Assignee: Aston University, Birmingham (GB)

(*) Notice: Subject to any disclaimer, the term of this patent is extended or adjusted under 35 U.S.C. 154(b) by 0 days.

(21) Appl. No.: 10/521,335

(22) PCT Filed: Jul. 23, 2003

(86) PCT No.: PCT/GB03/03256

§ 371 (c)(1),
(2), (4) Date: Jan. 10, 2005

(87) PCT Pub. No.: WO2004/008963

PCT Pub. Date: Jan. 29, 2004

(65) Prior Publication Data

US 2005/0244094 A1 Nov. 3, 2005

(30) Foreign Application Priority Data

Jul. 23, 2002 (EP) .................................. 02255134

(51) Int. Cl.
*G02B 6/00* (2006.01)

(52) U.S. Cl. ........................................................ 385/13
(58) Field of Classification Search ............... 356/73.1, 356/345, 352; 250/227.14, 227.23; 385/4, 385/14, 147; 705/2; 600/300
See application file for complete search history.

(56) References Cited

U.S. PATENT DOCUMENTS 4,669,814 A 6/1987 Dyott (Continued)

FOREIGN PATENT DOCUMENTS

EP 1372006 A1 * 12/2003

(Continued)

OTHER PUBLICATIONS

A. B. Lobo Ribeiro et al., "General error function of synthetic-heterodyne signal processing in interferometric fibre-optic sensors", International Journal of Optoetectronics, 1995, vol. 10, No. 3, XP-000587864, pp. 205-209.

(Continued)

*Primary Examiner*—Michelle Connelly-Cushwa
*Assistant Examiner*—Chris H. Chu
(74) *Attorney, Agent, or Firm*—Buckley, Maschoff & Talwalkar LLC

(57) ABSTRACT

Surface profiling apparatus (10) according to one embodiment comprises three long period gratings (LPGs) (12, 14, 16) fabricated in progressive three layered (PTL) fibre (18) and embedded within a deformable carrier member (40) comprising a skeleton (42) provided between two sheets of flexible rubber skin (44, 46). The LPGs (12, 14, 16) are illuminated by three wavelength modulated, narrow bandwidth optical signals, each having a different wavelength and modulation frequency. A photodetector (26) connected to three lock-in amplifiers (28, 30, 32) measures the amplitudes of the first and second harmonic frequency components of the photodetector output signal corresponding to each LPG (12, 14, 16). Similar surface profiling apparatus (10) forms the basis for respiratory function monitoring apparatus (100) in which five LPGs are provided within each of four PTL fibres (104, 106, 108, 110) and embedded in four carrier members (40a–d) attached to a garment (114) to be worn by a subject.

11 Claims, 15 Drawing Sheets

U.S. PATENT DOCUMENTS

| | | | |
|---|---|---|---|
| 4,807,950 A * | 2/1989 | Glenn et al. | 385/123 |
| 5,134,281 A | 7/1992 | Bryenton et al. | |
| 5,641,956 A | 6/1997 | Vengsarkar et al. | |
| 5,748,312 A * | 5/1998 | Kersey et al. | 356/478 |
| 5,754,293 A | 5/1998 | Farhadiroushan | |
| 5,920,582 A | 7/1999 | Byron | |
| 5,966,490 A | 10/1999 | Minns et al. | |
| 6,256,090 B1 * | 7/2001 | Chen et al. | 356/73.1 |
| 6,357,913 B1 | 3/2002 | Kim et al. | |
| 2004/0078219 A1 * | 4/2004 | Kaylor et al. | 705/2 |

FOREIGN PATENT DOCUMENTS

| | | |
|---|---|---|
| WO | WO 86/01303 A1 | 2/1986 |
| WO | WO 93/22624 * | 11/1993 |
| WO | WO 93/22624 A1 | 11/1993 |
| WO | WO 00/70307 * | 11/2000 |
| WO | WO 00/70307 A2 | 11/2000 |

OTHER PUBLICATIONS

S. K. Yao et al., "Microbending loss in a single-mode fiber in the pure-bend loss regime", Applied Optics, vol. 21, No. 17, Sep. 1, 1982, XP-001093774, pp. 3059-3060.

* cited by examiner

OPTICAL WAVEGUIDE BASED SURFACE PROFILING APPARATUS

This application is a U.S. National Stage filing under 35 U.S.C. §371 and 35 U.S.C §119, based on and claiming priority to PCT/GB03/03256 for "OPTICAL WAVEGUIDE BASED SURFACE PROFILING APPARATUS".

The invention relates to surface profiling apparatus and to respiratory function monitoring apparatus incorporating the surface profiling apparatus.

There are many situations in which there is a requirement to measure or monitor the shape or profile of a surface. An important example is the monitoring of respiratory function through non-invasive measurement of thoracoabdominal surface movement. Current approaches to carrying out volumetric measurement of respiratory function include inductance plethysmography in which a continuous, low-voltage electrical signal is passed through two coils of wire placed around a subject's rib cage and abdomen respectively. In this approach the changes in chest and abdomen volumes are taken to be equivalent to the changes in metric of the chest and abdomen compartments respectively. However, accurate calibration of this type of device is difficult and it gives a limited picture of the movements involved. Alternative approaches using cameras to record the movement of markers or grids of light on the chest have also been employed, but these are extremely complex techniques and they do not allow free ambulatory movement of the subject.

Various fibre-optic based devices have been developed which measure respiration according to the two degree of freedom system associated with inductance plethysmography. These devices perform measurements of the perimeter of the chest and abdomen, or depth of breathing, using optical fibre and fibre Bragg gratings as strain or displacement transducers. This technique ignores distortions which occur in the rib cage with increasing volumes of ventilation and relies on additional parameters which compensate for geometrical factors, cumulatively lumping them as part of coefficients in most cases as part of a calibration procedure.

Whilst these methods can typically provide accurate results (±5% error in tidal volume) for a single set of stationary quiet breathing conditions, accuracy is degraded with changes in posture as well as breathing pattern and magnitude. In validation studies of devices using these techniques, errors of as much as ±30% in respired tidal volume were not uncommon in a significant number of samples (up to 20% of the sample population). Such devices must also be re-calibrated frequently if the results produced are to be regarded as more than qualitative. As such they generally find application as monitors for recumbent patients, for example monitoring of sleep and postoperative apnoeas.

According to a first aspect of the invention there is provided surface profiling apparatus comprising:
 a first optical waveguide including a plurality of sensor sections in which a plurality of optical waveguide grating curvature sensing devices are respectively provided; and
 optical interrogation means operable to interrogate the optical waveguide grating curvature sensing devices, to determine the curvature experienced by each device, whereby a profile of a surface to which the sensor sections of the first optical waveguide are coupled may be constructed from the curvatures sensed by the optical waveguide grating curvature sensing devices.

The optical waveguide is preferably an optical fibre, which may be a silica-glass optical fibre or a polymer optical fibre.

The surface may be an exterior surface or may be an internal surface within a structure.

The first optical fibre preferably comprises a core, an inner cladding layer surrounding the core, and at least a first outer cladding layer surrounding the inner cladding layer, the refractive index of the inner cladding layer being less than the refractive index of the core, and the refractive index of the first outer cladding layer being less than the refractive index of the inner cladding layer.

Desirably, the first outer cladding layer is thick enough to isolate light propagating within a cladding mode of the inner cladding layer from a medium surrounding the first outer cladding layer. The first optical fibre may be progressive three layered optical fibre or matched index optical fibre.

The first optical fibre may further comprise a second outer cladding layer surrounding the first outer cladding layer in order to isolate light propagating within a cladding mode of the inner cladding layer from a medium surrounding the outermost cladding layer, the refractive index of the second outer cladding layer being less than the refractive index of the first outer cladding layer. The first optical fibre may comprise a plurality of outer cladding layers, each outer cladding layer surrounding a preceding outer cladding layer and having a lower refractive index than the preceding outer cladding layer.

The refractive index profile of the fibre core may be radially asymmetric. Alternatively or additionally the refractive index profile of one or more cladding layers of the fibre may be radially asymmetric.

The surface profiling apparatus may further comprise an optical waveguide strain sensor, and most preferably further comprises a plurality of optical waveguide strain sensors. One or more optical waveguide strain sensors may be provided within the first optical waveguide. A strain sensor is preferably provided between a or each pair of optical waveguide grating curvature sensing devices.

One or more optical waveguide strain sensors may alternatively or additionally be provided within a second optical waveguide, which may be a second optical fibre. A strain sensor may be provided between a or each pair of optical waveguide grating curvature sensing devices. Alternatively or additionally, a strain sensor may be provided generally adjacent to, and generally parallel with, a or each optical waveguide grating curvature sensing device.

The first optical fibre may alternatively comprise an asymmetric optical fibre, which may have a radially asymmetric core or a radially asymmetric cladding layer. The first optical fibre is preferably D-shaped optical fibre.

The surface profiling apparatus may further comprise an optical waveguide strain sensor provided within a second optical waveguide. The surface profiling apparatus preferably comprises a plurality of optical waveguide strain sensors, which may be provided within a plurality of second optical waveguides. The or each second optical waveguide may comprise a second optical fibre. A strain sensor may be provided between a or each pair of optical waveguide grating curvature sensing devices. Alternatively or additionally, a strain sensor may be provided generally adjacent to, and generally parallel with, a or each optical waveguide grating curvature sensing device.

The or each optical waveguide strain sensor is preferably an optical waveguide grating strain sensor, and is most preferably a Bragg grating.

A plurality of first optical waveguides including a plurality of sensor sections may be provided.

The optical waveguide grating curvature sensing devices preferably comprise optical waveguide grating devices. An optical waveguide grating device may comprise a long period grating. The long period grating may be radially asymmetric. The long period grating may include one or more phase-shifts within its periodic refractive index variation. Alternatively or additionally the period of the refractive index variation of one or more parts of the long period grating may be chirped.

An optical waveguide grating device may alternatively comprise two long period gratings arranged to together define an in-line Mach-Zehnder interferometer. An optical waveguide grating device may further alternatively comprise an optical waveguide Bragg grating. The Bragg grating may be a chirped Bragg grating. Alternatively, or additionally, the amplitude of the periodic refractive index variation of the Bragg grating may be tapered and/or apodised. An optical waveguide grating device may further alternatively comprise two optical waveguide Bragg gratings arranged to together define a Fabry-Perot etalon.

The surface profiling apparatus may further comprise coupling means for coupling the sensor sections of the first optical waveguide to the surface to be profiled. The surface profiling apparatus may further comprise additional coupling means for coupling the or each optical waveguide strain sensor to the surface to be profiled. A coupling means preferably comprises a carrier member, one or more sensor sections of the optical waveguide or one or more optical waveguide strain sensors being fixed to or embedded within a carrier member. The coupling means may alternatively comprise a plurality of carrier members mounted on a support structure, one or more optical waveguide sensor sections or one or more optical waveguide strain sensors being fixed to or embedded within each carrier member. The or each carrier member is preferably deformable and most preferably comprises a flexible skin fixed to a partially rigid, expandable skeleton structure. The carrier member or support structure is preferably of a corresponding size and shape to the surface to be profiled, such that a close fit is provided between the or each carrier member and the surface.

The optical interrogation means is preferably a derivative spectroscopy or synthetic heterodyne based optical interrogation means operable to detect changes in the spectral profile of an optical waveguide grating curvature sensing device. The optical interrogation means preferably comprises an optical source operable to generate a wavelength modulated optical signal at a wavelength within the spectral range of an optical waveguide grating curvature sensing device to be interrogated, the optical source being optically coupled to one, input, end of the respective optical waveguide, and optical detection means optically coupled to the other, output, end of the optical waveguide and being operable to detect changes in the spectral transmission profile of the optical waveguide grating curvature sensing device being interrogated and to thereby determine the curvature experienced by the grating curvature sensing device.

The optical signal preferably has a narrow spectral bandwidth compared with the spectral bandwidth of the optical waveguide grating curvature sensing device to be interrogated.

The optical interrogation means is preferably further operable to interrogate the or each optical waveguide strain sensor, to determine the strain experienced by each strain sensor. The optical interrogation means may further comprise a second optical detection means optically coupled to the input end of the optical waveguide and being operable to detect changes in the spectral reflection profile of an optical waveguide strain sensor being interrogated, to thereby determine the strain experienced by the strain sensor.

The optical source may comprise a plurality of wavelength modulated lasers, the wavelength of each laser output optical signal lying within the spectral range of its respective optical waveguide grating curvature sensing device or optical waveguide strain sensor. One or each of the wavelength modulated lasers may be distributed feedback lasers, the injection current provided to the laser from its drive unit being modulated at a desired frequency to thereby produce a wavelength modulation on the optical output signal generated by the laser. One or each of the wavelength modulated lasers may alternatively comprise fibre lasers having a fibre Bragg grating for one or both of the laser mirrors, the or each fibre Bragg grating being coupled to tuning means operable to vary the resonant wavelength of the or each fibre Bragg grating at a desired modulation frequency, thereby apply a corresponding wavelength modulation to the laser output signal.

The optical source may alternatively or additionally comprise a plurality of fibre Bragg gratings, each grating having a different resonant wavelength lying within the spectral profile of a respective optical waveguide grating curvature sensing device or optical waveguide strain sensor, and being coupled to tuning means operable to vary its resonant wavelength at a desired modulation frequency, and a broad bandwidth optical source for illuminating the gratings, the light reflected by each grating thereby forming a wavelength modulated narrow bandwidth optical signal. The broad bandwidth optical source may be a superluminescent light emitting diode or an edge-emitting light emitting diode.

Preferably, a different modulation frequency is used for each optical waveguide grating curvature sensing device or optical waveguide strain sensor provided in a single optical waveguide.

The optical source may further alternatively comprise a wavelength tunable optical source, operable to generate a narrow bandwidth optical signal, and wavelength modulation apparatus operable to apply a wavelength modulation at a desired modulation frequency to the generated optical signal. The wavelength tunable optical source may be a distributed feedback laser or a Fabry-Perot etalon based laser.

The optical detection means preferably comprises:
a first photodetector optically coupled to the output end of the or each optical waveguide; and
a plurality, corresponding to the number of optical waveguide grating curvature sensing devices provided within the respective waveguide, of lock-in amplifiers or synchronous detectors each operable to measure the amplitude of a detected optical signal at the modulation frequency associated with a particular optical waveguide grating curvature sensing device and a harmonic of the modulation frequency, most preferably the second harmonic.

The optical interrogation means may additionally comprise second optical detection means, in the form of a second photodetector, optically coupled to the input end of the optical waveguide.

The optical detection means preferably further comprises data processing means connected to the or each first photodetector, operable to calculate the ratio of the amplitudes. The data processing means is desirably further operable to calculate the are tangent of the ratio of the amplitudes, to which the curvature experienced by an optical waveguide grating curvature sensing device under interrogation is linearly related.

The optical interrogation means may alternatively comprise:

a broadband optical source operable to generate a broad bandwidth optical signal having a spectral bandwidth encompassing the spectral profile of an optical waveguide grating curvature sensing device or optical waveguide strain sensor to be interrogated, the optical source being optically coupled to one, input, end of the respective optical waveguide; and optical detection means optically coupled to the other, output, end of the optical waveguide.

The optical interrogation means may additionally comprise second optical detection means optically coupled to the input end of the optical waveguide. The optical detection means preferably comprises an optical spectrum analyser operable to record the spectral profile of the optical waveguide grating curvature sensing device or optical waveguide strain sensor under interrogation and data processing means, such as a microprocessor or personal computer, operable to match the recorded spectral profile with one of a plurality of pre-recorded spectral profiles, to thereby determine the curvature or strain experienced by the grating device under interrogation.

The optical spectrum analyser and the data processing means are preferably portable.

The data processing means is preferably further operable to generate a two-dimensional or three-dimensional wire-frame profile of the surface being interrogated from the curvature values. The data processing means is preferably additionally operable to generate a two-dimensional or three-dimensional wire-frame profile of the surface being interrogated from the curvature values and the strain values.

According to a second aspect of the invention there is provided respiratory function monitoring apparatus comprising surface profiling apparatus according to the first aspect of the invention.

Preferably, the support structure of the coupling means comprises a garment of a size and shape suitable to closely fit across at least part of the thoracoabdominal surface of a subject whose respiratory function is to be monitored.

The data processing means is preferably operable to generate a 2- or 3-dimensional wire-frame image of the thoracoabdominal surface of a subject wearing the respiratory function monitoring apparatus, and is most preferably operable to repeatedly generate the image in real time, to thereby generate a changing, updating image of the thoracoabdominal surface.

Embodiments of the invention will now be described in detail, by way of example only, with reference to the accompanying drawings, in which.

Figure 19:
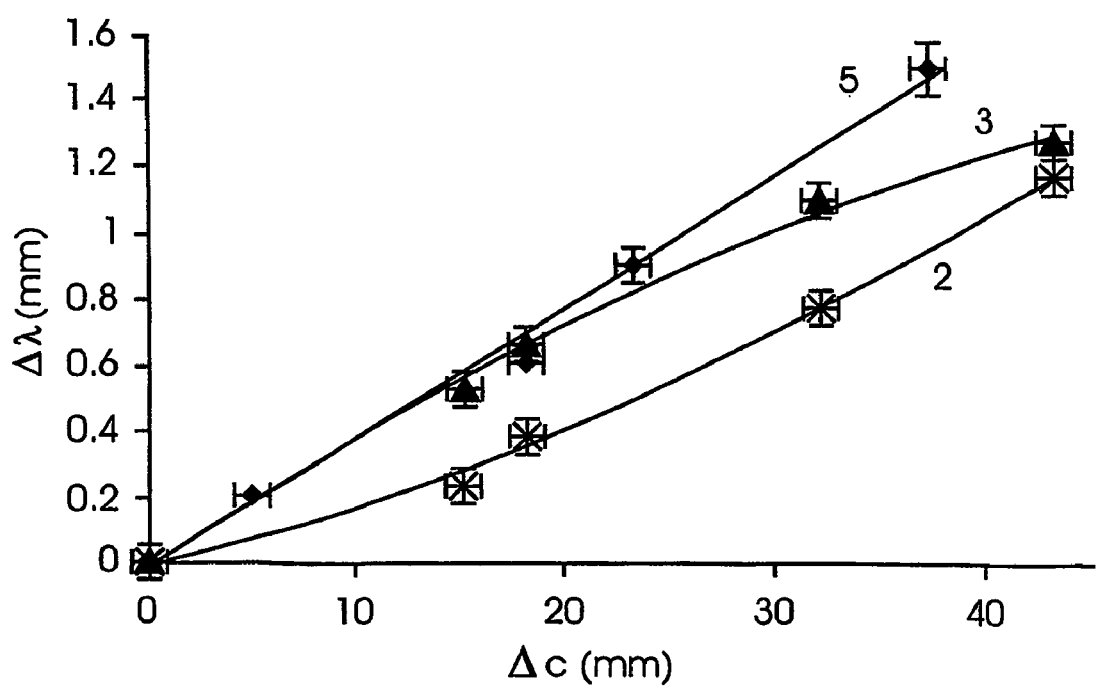
Figure 20:
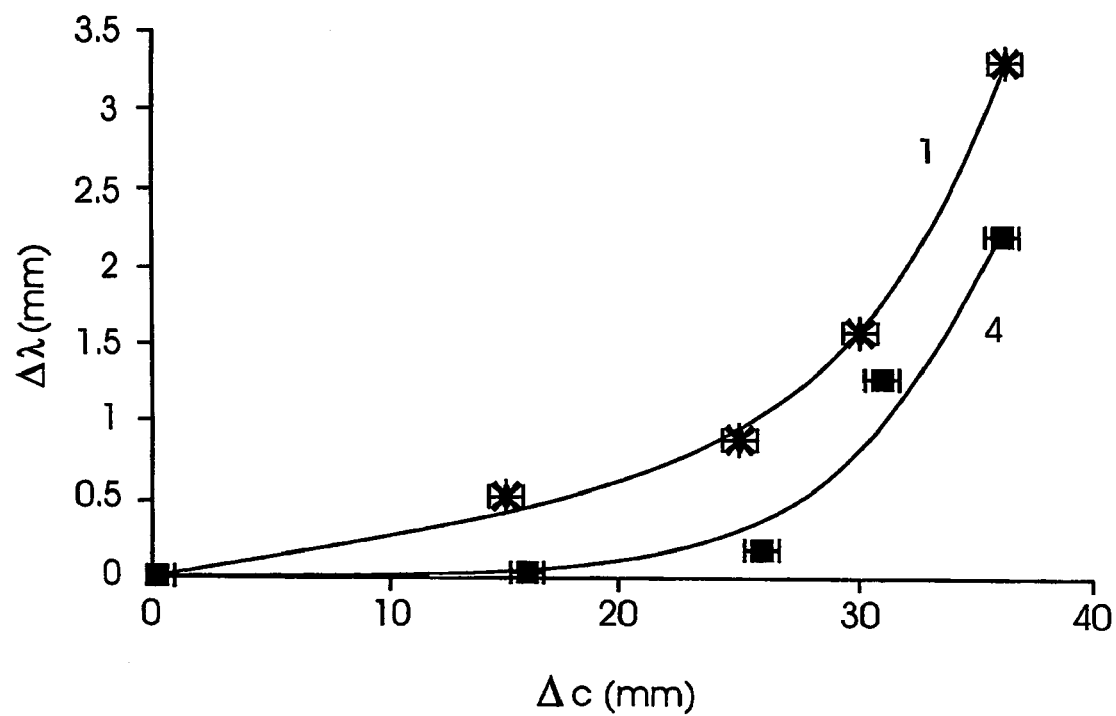

FIG. 19 shows the change in the central wavelength ($\Delta\lambda$) of the LPG's attenuation band as a function of the change in the circumference ($\Delta c$) of the torso, for the carrier member located on the lower chest (positions 2, 3 & 5); and FIG. 20 shows the change in the central wavelength ($\Delta\lambda$) of the LPG's attenuation band as a function of the change in the circumference ($\Delta c$) of the torso, for the carrier member located on the upper chest (positions 1 & 4).

Referring to FIGS. 1 to 9, a first embodiment of the invention provides surface profiling apparatus 10 utilising optical waveguide grating devices in the form of long period gratings (LPGs) 12, 14, 16 provided within respective sensing sections of single mode progressive three layered (PTL) optical fibre 18. Only three LPGs provided within a single carrier member are shown here for clarity but it will be appreciated that a larger number of LPGs may be used and may be provided within one or more carrier members.

LPGs consist of a periodic refractive index variation produced within the core of an optical fibre. The refractive index variation is induced within the fibre as a result of exposure of the fibre to ultra-violet radiation. The period of the refractive index variation is typically between 100 µm and 600 µm, and is much greater than the guided wavelength. An LPG acts to couple light incident on it from the fibre core into the fibre cladding, thereby producing attenuation bands within the transmission spectrum of the optical fibre. Light is coupled from the core into the cladding with a spectral selectivity that is closely determined by the periodicity of the refractive index variation.

LPGs are sensitive to strain ($\epsilon$), temperature (T) and the refractive index ($n_S$) of the surrounding medium. The sensitivity of an LPG to these parameters can manifest itself in two different ways: the central wavelength of the attenuation band can shift in wavelength; and a change in the spectral transmission profile of the attenuation band can occur. Of particular interest here is the sensitivity of LPGs to bending, which induces both a wavelength shift and a change in the spectral profile of the attenuation band.

The wavelength shift of the attenuation band arises as a result of the phase match condition of an LPG, which determines the spectral position of the attenuation band, and is given by $$[n(co)_{eff}(\lambda,T,\lambda)-n^v(cl)_{eff}(\lambda,T,n_S,\epsilon)]\cdot\Lambda(T,\epsilon)=\Delta n_{eff}\Lambda(T,\epsilon)=\lambda \quad (1)$$

where $\Lambda$ is the period of the grating, $n(co)_{eff}$ is the effective refractive index of the core mode and $n^v(cl)_{eff}$ is the effective refractive index of the $v^{th}$ radial cladding mode, both indices also being dependent on the refractive indices of the core and cladding, and on wavelength $\lambda$.

The magnitude of the wavelength shift induced by an applied strain, or a change in temperature or the refractive index of the surrounding medium, is dependent on the difference between the effective refractive indices of the core and the $v^{th}$ radial cladding mode, and on the difference between the group effective refractive indices of the core and $v^{th}$ radial cladding modes. The wavelength sensitivity of LPGs to bending arises from their sensitivity to strain. Bending an optical fibre induces strain and compression in the fibre, which in turn changes the group effective refractive indices of the core and the $v^{th}$ radial cladding mode as well as $n(co)_{eff}$ and $n^v(cl)_{eff}$.

Figure 1:
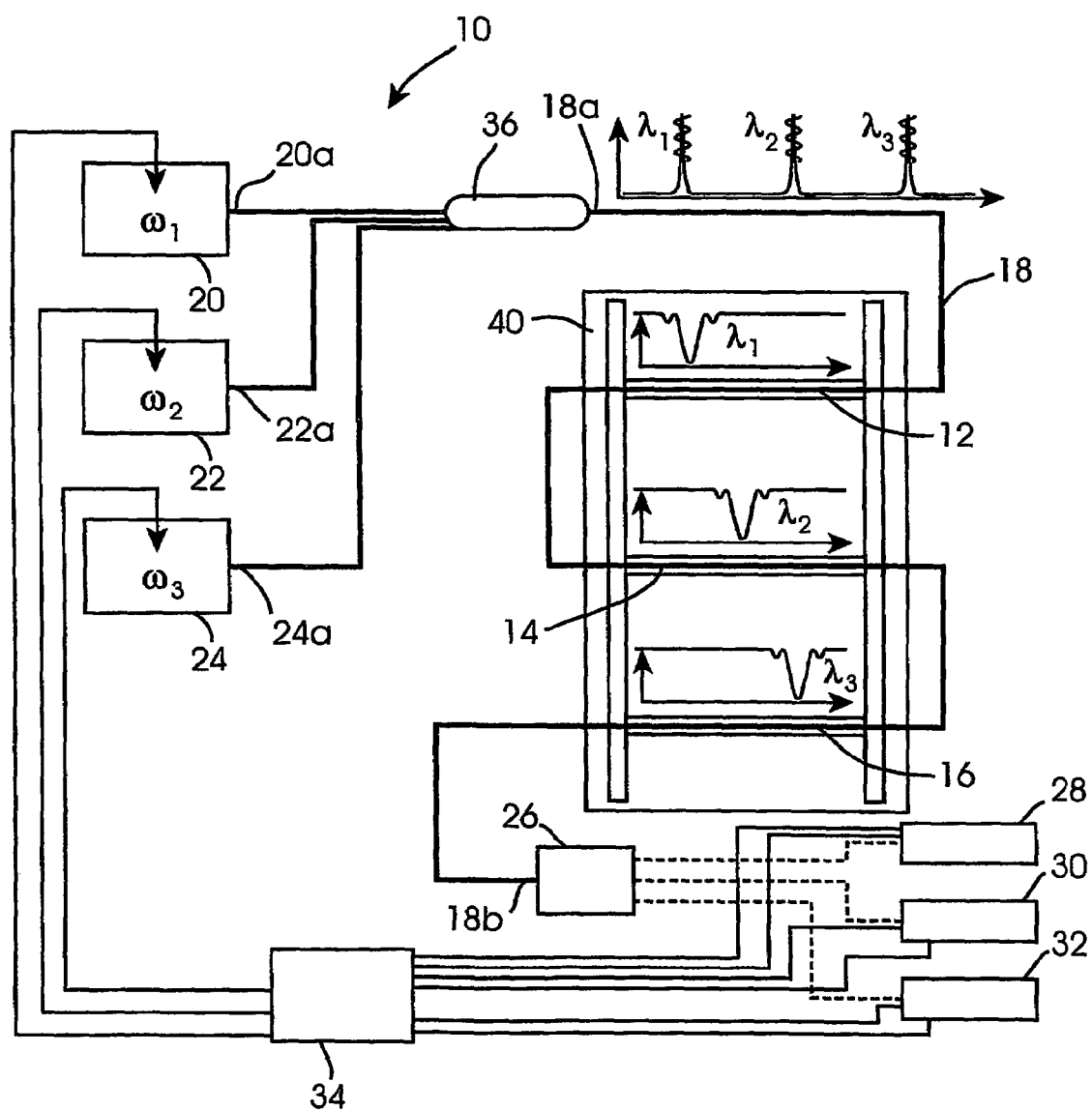
FIG. 1 is a schematic representation of surface profiling apparatus according to a first embodiment of the invention.

In the embodiment shown in FIG. 1, the first LPG 12 has a period of 240 µm, a length of 8 cm and a strength of ~14 dB, the second LPG 14 has a period of 480 µm, a length of 10 cm and a strength of a ~10 dB, and the third LPG 16 has a period of 350 µm, a length of 10 cm and a strength of ~10 dB. The LPGs 12, 14, 16 were fabricated using the point-to-point fabrication technique which will be well known to the skilled person and so will not be described in detail here. The PTL fibre used was not specifically designed to be photosensitive and so its photosensitivity was increased by hydrogenation at a pressure of 120 Bar for a period of 2 weeks at room temperature.

The periods of the LPGs 12, 14, 16 were chosen so that the associated cladding modes of the attenuation bands were from modes $n_{cl}(1,1)$ to $n_{cl}(1,10)$, which are known to be insensitive to the refractive index $n_s$ of the surrounding medium.

The first LPG 12 produces an attenuation band having a central wavelength of ~1536 nm, associated with its $9^{th}$ cladding mode, the second LPG 14 produces an attenuation band having a central wavelength of ~1522 nm, associated with its $5^{th}$ cladding mode, and the third LPG 16 produces an attenuation band having a central wavelength of ~1520 nm, associated with its 4th cladding mode.

Figure 2:
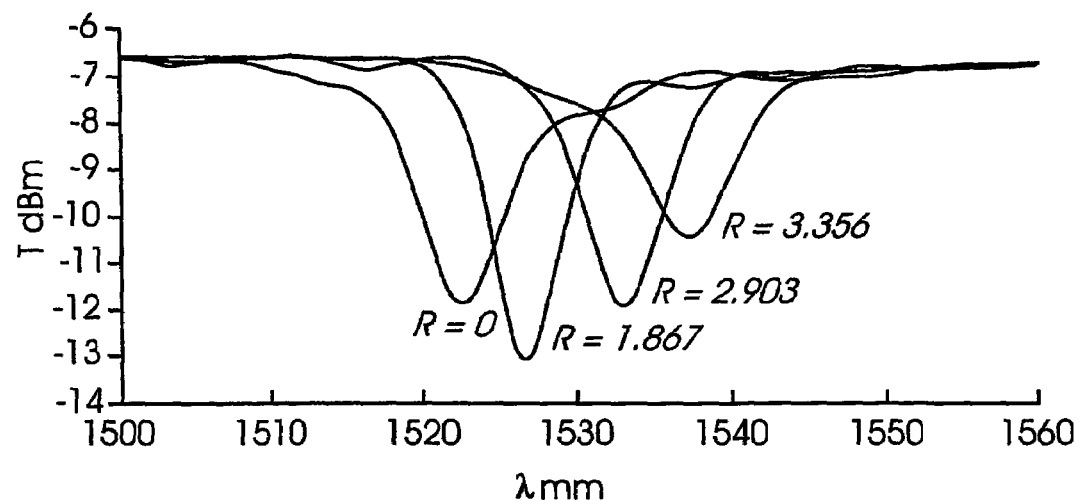
FIG. 2 illustrates the effect on the transmission spectrum of a long period grating (period 480 µm) of the application of various curvatures ($C m^{-1}$) to the grating.

FIG. 2 shows how the optical transmission spectrum (T) of the second LPG 14 changes as the radius of curvature applied to the LPG 14 is increased from 0 to 3.356 m$^{-1}$.

In this example, the optical interrogation means takes the form of three distributed feedback (DFB) lasers 20, 22, 24 optically coupled to the input end 18a of the PTL fibre 18.

The DFB lasers 20, 22, 24 are thermally stabilised and optical fibre pigtailed, and are operable to generate wavelength modulated, narrow bandwidth (i.e. narrow with respect to the spectral bandwidths of the LPGs 12, 14, 16 to be interrogated) optical signals. Both the wavelength of the optical signal generated by each DBF laser 20, 22, 24 and the frequency of the applied wavelength modulation are different for each DFB laser 20, 22, 24, and thus each respective LPG 12, 14, 16. The wavelength of each optical signal is selected to be close to the resonant wavelength of the respective LPG 12, 14, 16. The output fibre pigtails 20a, 22a, 24a of the DFB lasers 20, 22, 24 are optically coupled to the PTL fibre 18 via a 3×1 optical fibre multiplexer 36. A photodetector 26 is optically coupled to the output end 18b of the PTL fibre 18. The electrical output of the photodetector 26 is connected to three lock-in amplifiers 28, 30, 32. The different wavelength modulation frequencies are used to identify the LPG 12, 14, 16 which each part of the output signal generated by the photodetector 26 relates to, as will described in more detail below.

The first DFB laser 20 generates a narrow bandwidth optical signal having a wavelength $\lambda_1$ of ~1532 nm. An electrical sinusoidal modulation signal of a frequency $\omega_1$ of 5 kHz, generated by a signal generator 34, is applied to the laser injection current to thereby apply a sinusoidal wavelength modulation, having a first harmonic frequency of 5 kHz and an amplitude of 0.06 nm, to the optical signal. Modulating the wavelength at a particular modulation frequency $\omega_1$ generates wavelength modulations on the optical signal at a series of harmonics of the modulation frequency i.e. $\omega_1, 2\omega_1$ etc. The second DFB laser 22 generates a narrow bandwidth optical signal having a wavelength $\lambda_2$ of ~1517 nm. An electrical sinusoidal modulation signal of a frequency $\omega_2$ of 3.7 kHz, generated by the signal generator 34, is applied to the laser injection current to thereby produce a sinusoidal wavelength modulation having a first harmonic frequency of 3.7 kHz and an amplitude of 0.06 nm. The third DFB laser 24 generates a narrow bandwidth optical signal having a wavelength $\lambda_3$ of ~1415 nm. An electrical sinusoidal modulation signal of a frequency $\omega_3$ of 2.3 kHz, generated by the signal generator 34, is applied to the laser injection current to thereby produce a sinusoidal wavelength modulation having a first harmonic frequency of 2.3 kHz and an amplitude of 0.06 nm. The drive current is set to operate in the saturation regimes of the DFB lasers 20, 22, 24 where the current induced amplitude modulation is minimised.

The series of wavelength modulation frequency harmonics present on each optical signal give rise to corresponding frequency components in the electrical output signal from the photodetector 26. The in-phase component of the $n^{th}$ harmonic frequency component of the photodetector output signal is proportional to the $n^{th}$ derivative of the spectral profile under interrogation. That is to say, the amplitudes of the first and second harmonic frequency components ($\omega_1$ and $2\omega_1$, $\omega_2$ and $2\omega_2$, and $\omega_3$ and $2\omega_3$) of the photodetector output signal are proportional to the first and second derivatives of the spectral transmission profiles of the respective LPGs 12, 14, 16.

Figure 3:
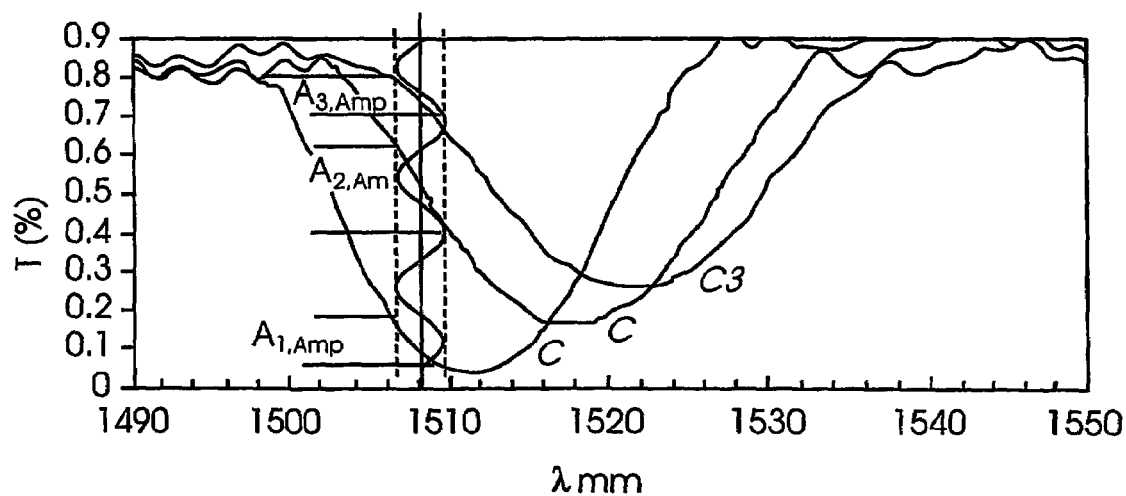
FIG. 3 shows the attenuation profile of an optical waveguide grating device in the form of a long period grating for three different applied curvatures ($C_1$, $C_2$ and $C_3$) together wavelength modulation range of a wavelength modulated narrow bandwidth optical signal.
Figure 4:
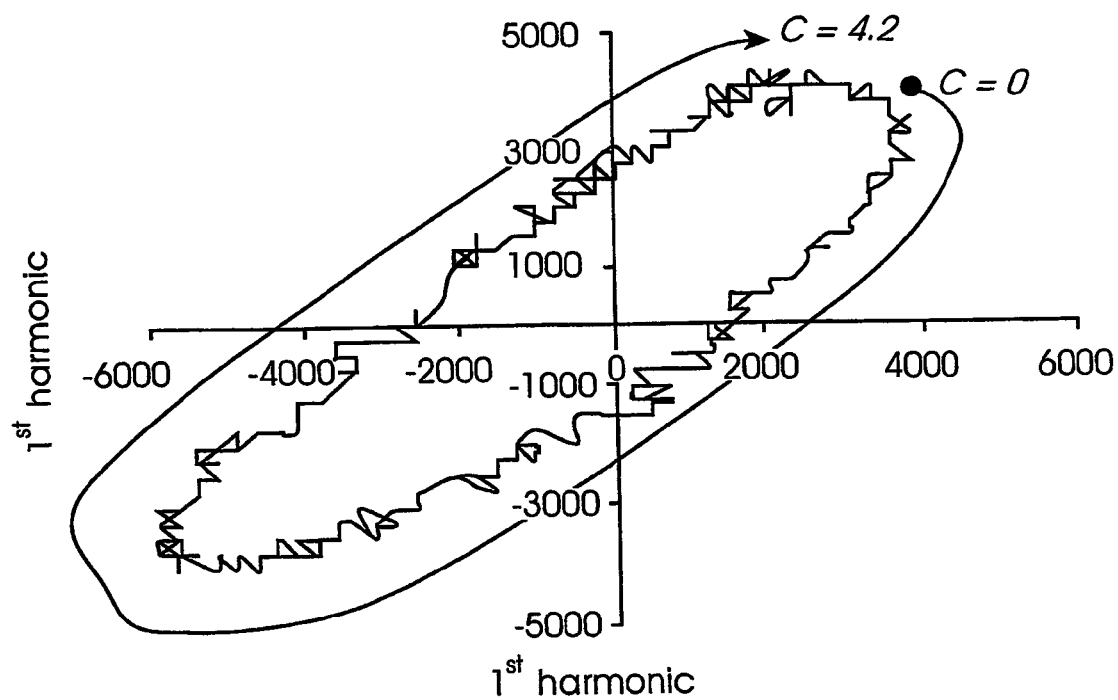
FIG. 4 shows a parametric plot of the first and second harmonics of the wavelength modulation frequency for various curvatures applied to a long period grating.

FIG. 3 shows the attenuation profiles (percentage of transmission power (T) as a function of wavelength ($\lambda$)) of an LPG for three different curvatures ($C_1$, $C_2$, and $C_3$), together with the wavelength modulation 38 at frequency $\omega$ of a DFB laser, which may be given by:

$$\lambda_{DFB}=\lambda_0+\delta\lambda\sin(\omega t)$$

It can be seen in FIG. 3 that the amplitude $A_1$, $A_2$, and $A_3$ of the photodetector output signal at frequency ω varies with the amount of curvature applied to the LPG.

In addition to the signals at modulation frequencies $\omega_1$, $\omega_2$ and $\omega_3$, the signal generator 34 also generates sinusoidal electrical signals at the second harmonics of the modulation frequencies i.e. at $2\omega_1$, $2\omega_2$ and $2\omega_3$. The electrical signals generated by the signal generator 34 at frequencies $\omega_1$ and $2\omega_1$ are passed to the first lock-in amplifier 28, the electrical signals at $\omega_2$ and $2\omega_2$ are passed to the second lock-in amplifier 30, and the electrical signals at $\omega_3$ and $2\omega_3$ are passed to the third lock-in amplifier 32. The lock-in amplifiers 28, 30, 32 are thereby set to measure the amplitudes of the first and second harmonic frequency components of the photodetector output signal corresponding to the first LPG 12, the second LPG 14 and the third LPG 16 respectively.

The ratio of the first and second derivatives is a unique function of position within the spectral transmission profile and is independent of any attenuation which may occur within the optical system. The amplitudes of the first and second harmonic frequency components can be represented by:

$$Amp^{1st} = A\sin(\zeta) \text{ and } Amp^{2nd} = B\sin(\zeta + \alpha)$$

where $\zeta$ represents the degree of curvature experience by an LPG under interrogation and $\alpha$ is the relative phase difference between the first and second harmonics. The ratio of the amplitudes of the harmonics is unique for a given radius of curvature, as illustrated in the parametric plot of the first and second harmonics recorded for radii of curvature of between 0 and 4.20 m$^{-1}$ shown in FIG. 4.

Figure 5:
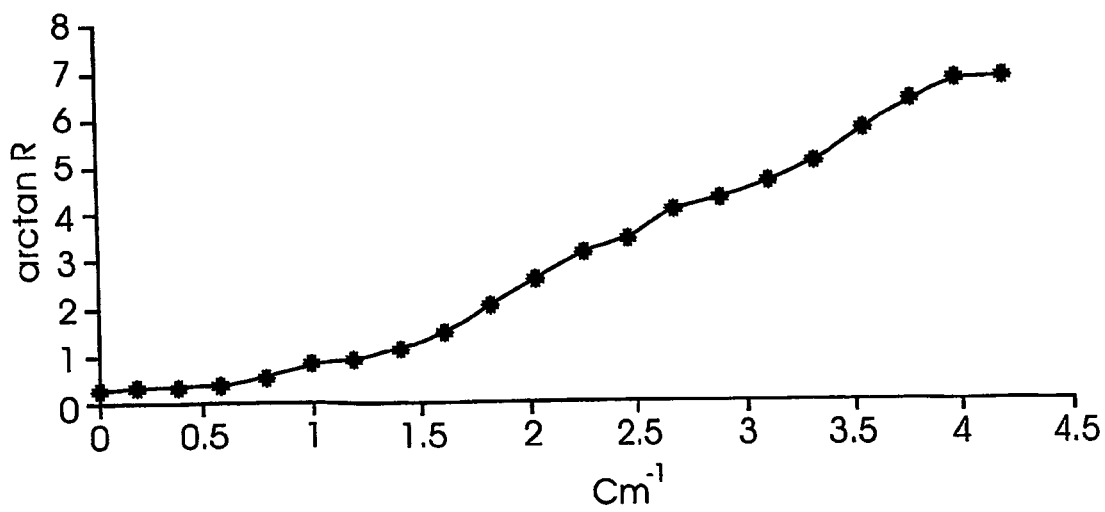
FIG. 5 shows the arctan of the ratio (R) of the amplitudes of the first and second harmonics of the wavelength modulation frequency as a function of radius of curvature (C) for a long period grating of period 240 µm.
Figure 6:
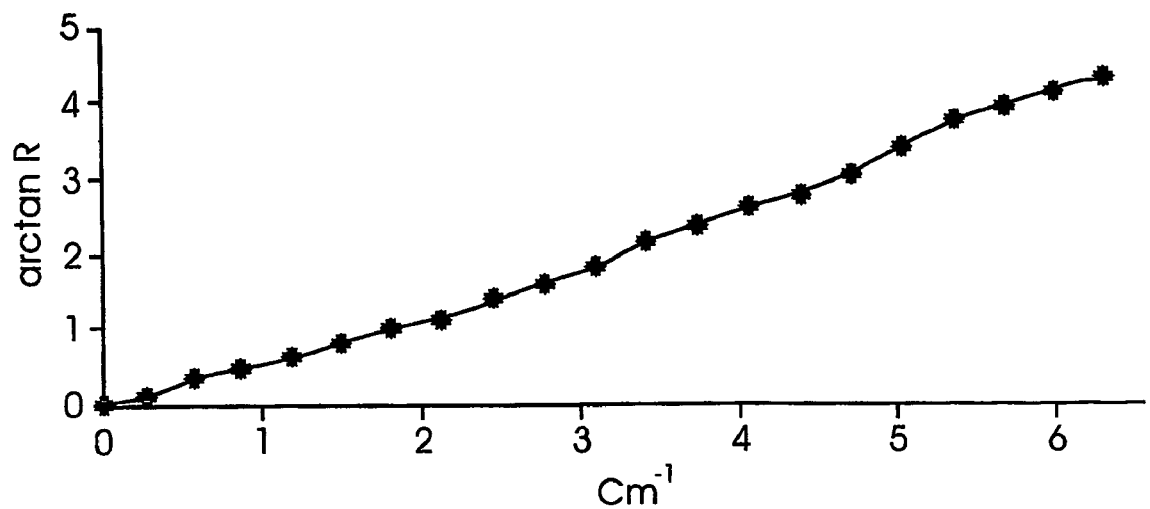
FIG. 6 shows the arctan of the ratio (R) of the amplitudes of the first and second harmonics of the wavelength modulation frequency as a function of radius of curvature (C) for a long period grating of period 480 µm.

A more useful relationship between the amplitudes of the first and second harmonic frequency components of the photodetector output signal and the radius of curvature applied to an LPG is produced by taking the inverse tangent (arctan) of the ratio of the amplitudes of the first and second harmonics. This yields an approximately linear relationship between the arctan of the ratio of amplitudes and the radius of curvature, as shown in FIGS. 5 and 6 for the first LPG 12 and the second LPG 14 respectively. A radius of curvature resolution of +/−0.05 m$^{-1}$ and a curvature measurement range of ~+/−3 m$^{-1}$ is available in this example.

Figure 9:
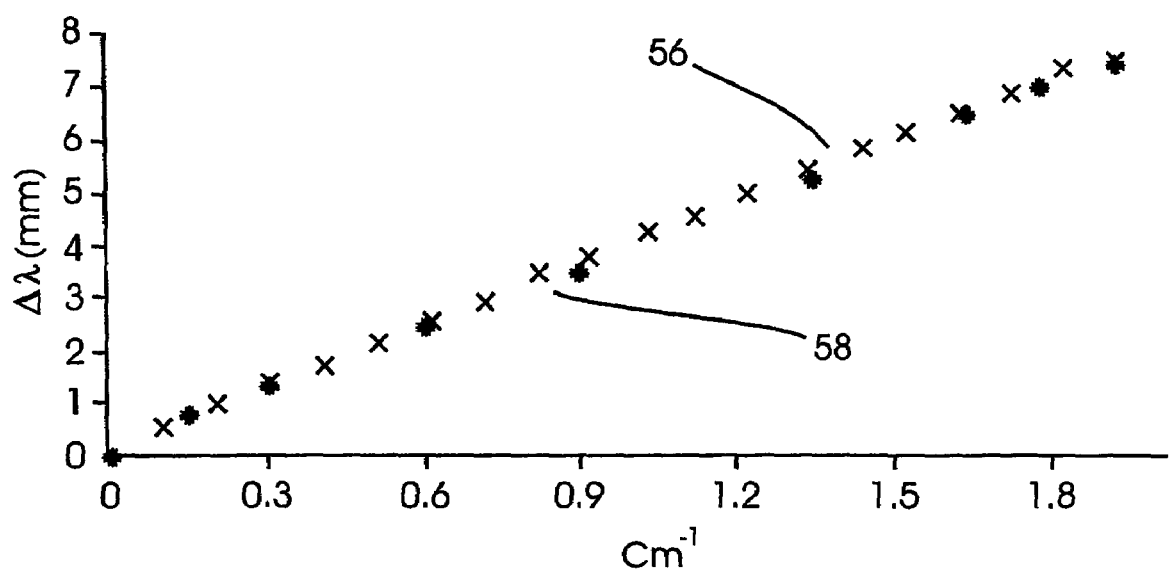
FIG. 9 shows the central wavelength of the attenuation band ($4^{th}$ mode) of the third LPG 16 (period 350 µm) as a function of radius of curvature.

The spectral sensitivity $$\frac{d\lambda}{dR}$$

of the third LPG 16, i.e. the change in the central wavelength (Δλ) of the attenuation band associated with the fourth cladding mode, as a function of radius of curvature (R) is 3.747±0.002 nm.m, and is a linear relationship, as shown in FIG. 9. The theoretically predicted wavelength shift is given by:

$$\Delta\lambda = \left[\frac{\Lambda\lambda}{(\delta n_{\mathit{eff}} - \delta n_g)} \cdot \frac{d\delta n_{\mathit{eff}}}{dR} + \frac{(\delta n_{\mathit{eff}})^3}{\delta n_g} \frac{d\Lambda}{dR}\right] \cdot \Delta R, \quad (2)$$

where $\delta n_{\mathit{eff}} = n_{co\mathit{eff}} - n_{cl\mathit{eff}_v}$ is the differential effective index between the cladding and the core mode and $\delta n_g = n_{co_g} - n_{cl_{g_v}}$ is the differential group index. The effective refractive indices of the core and 4$^{th}$ cladding mode are calculated as a function of curvature using a 2-D curvilinear hybrid mode eigenvalue equation. It is assumed that the amount of birefringence induced in a typical single mode fibre is negligibly small for curvatures of <2 m$^{-1}$, so no birefringence induced splitting of the attenuation band will occur. FIG. 9 demonstrates reasonable agreement between the theoretical wavelength shift values 56 calculated at a number of different curvatures and the experimentally measured values 58.

Figure 7:
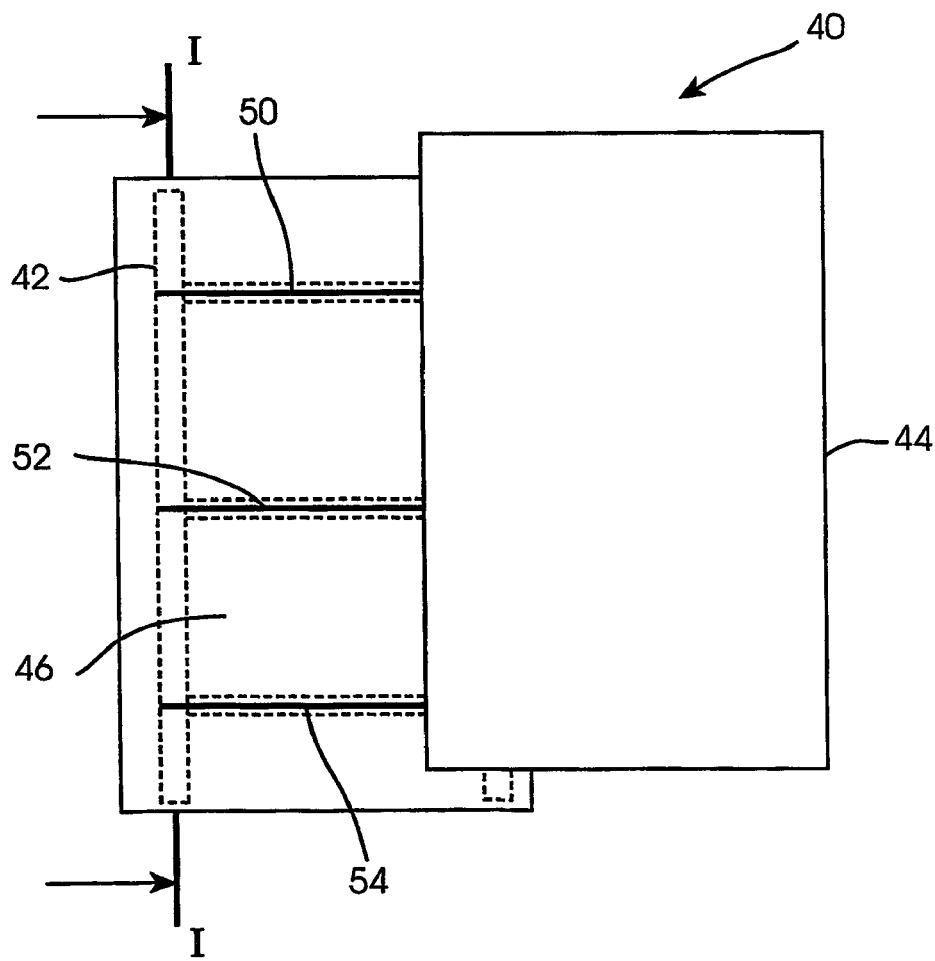
FIG. 7 is a diagrammatic partially exploded plan view of a carrier member suitable for use with the apparatus of FIG. 1.
Figure 8:
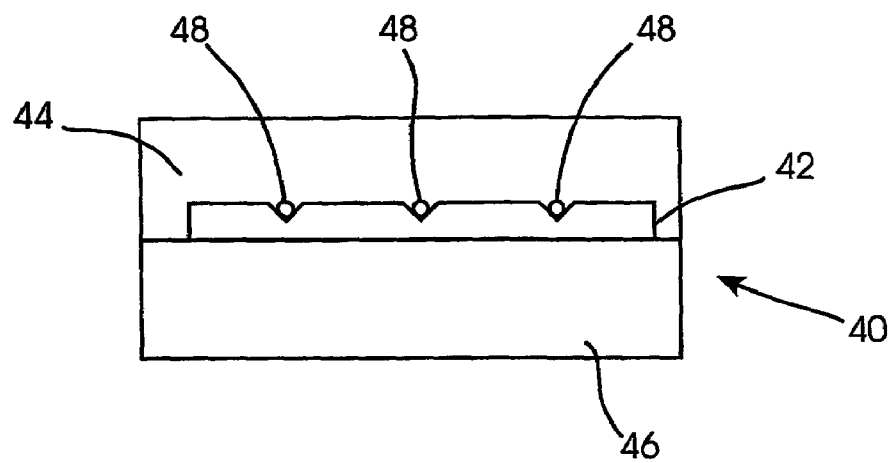
FIG. 8 is a diagrammatic sectional view along the line A—A of FIG. 7.

In this embodiment the LPGs 12, 14, 16 are embedded within a carrier member 40, shown in FIGS. 1, 7 and 8. The carrier member 40 is deformable and takes the form of a skeleton 42 embedded between two sheets of flexible rubber skin 44, 46. The lower skin 46, which will be in contact with the surface to be profiled, comprises a sheet (length 250 mm, width 120 mm and thickness 2 mm) of natural latex rubber. This provides a flexible stage which is also thermally insulating. The upper skin 44 comprises a room temperature vulcanising clear silicon rubber (n>1.5), and has a thickness of approximately 3 mm.

The skeleton 42 is partially rigid, but expandable, and is constructed from strips 50, 52, 54 (length 200 mm, width 12 mm, and thickness 0.254 mm) of carbon steel, which support the sensing sections of the PTL fibre 18 containing the LPGs 12, 14, 16. The support strips 50, 52, 54 are fixed to the lower skin 46 and are arranged parallel to one another, approximately 75 mm apart. Two connecting strips 56 (length 80 mm) are provided at either end of the support strips 50, 52, 54. V-section grooves 48 are formed along the length of the support strips 50, 52, 54 for receiving the sensing sections of the PTL fibre 18. The fibre is fixed to the support strips 50, 52, 54 using a cyanoacrylate adhesive. The v-grooves 48 minimise bending of the LPGs 12, 14, 16 during the gluing process. The steel skeleton 42 gives longitudinal rigidity to the carrier member 40 and prevents the LPGs 12, 14, 16 from experiencing significant axial strain during use.

The steel skeleton also acts to stabilise the temperature of the LPGs 12, 14, 16. Over a 15° C. temperature range the central wavelength of the attenuation mode associated with the 4$^{th}$ cladding mode of the third LPG 16 was observed to shift by 0.36 nm. This gives a temperature sensitivity of $$\frac{d\lambda}{dT} = 2.3 \pm 0.1 \times 10^{-2} \text{ nm}°\text{C}^{-1}$$

Comparing this with a known temperature sensitivity of 0.198 nm° C.$^{-1}$ for the same cladding mode in bare PTL fibre, indicates that the temperature sensitivity of the LPGs 12, 14, 16 mounted on the carbon steel support strips 50, 52, 54 is approximately an order of magnitude smaller than that of bare PTL fibre. This reduction in temperature sensitivity of the LPGs 12, 14, 16 is due to the LPGs taking on the thermal expansion properties of the support strips.

In use, the carrier member 40 is placed on the surface to be profiled, with the lower skin 46 in contact with the surface. The radius of curvature of the surface at various monitoring locations is measured by the LPG provided at the respective monitoring location. The radius of curvature values measured by each LPG are input into a surface-modelling algorithm which creates a 2-dimensional or 3-dimensional wire-frame profile of the surface under investigation. By continually or repeatedly measuring the radius of curvature at each of the monitoring locations any changes in the profile of the surface can be monitored. Movement of the surface at one or more of the monitoring locations can also be tracked.

Figure 10:
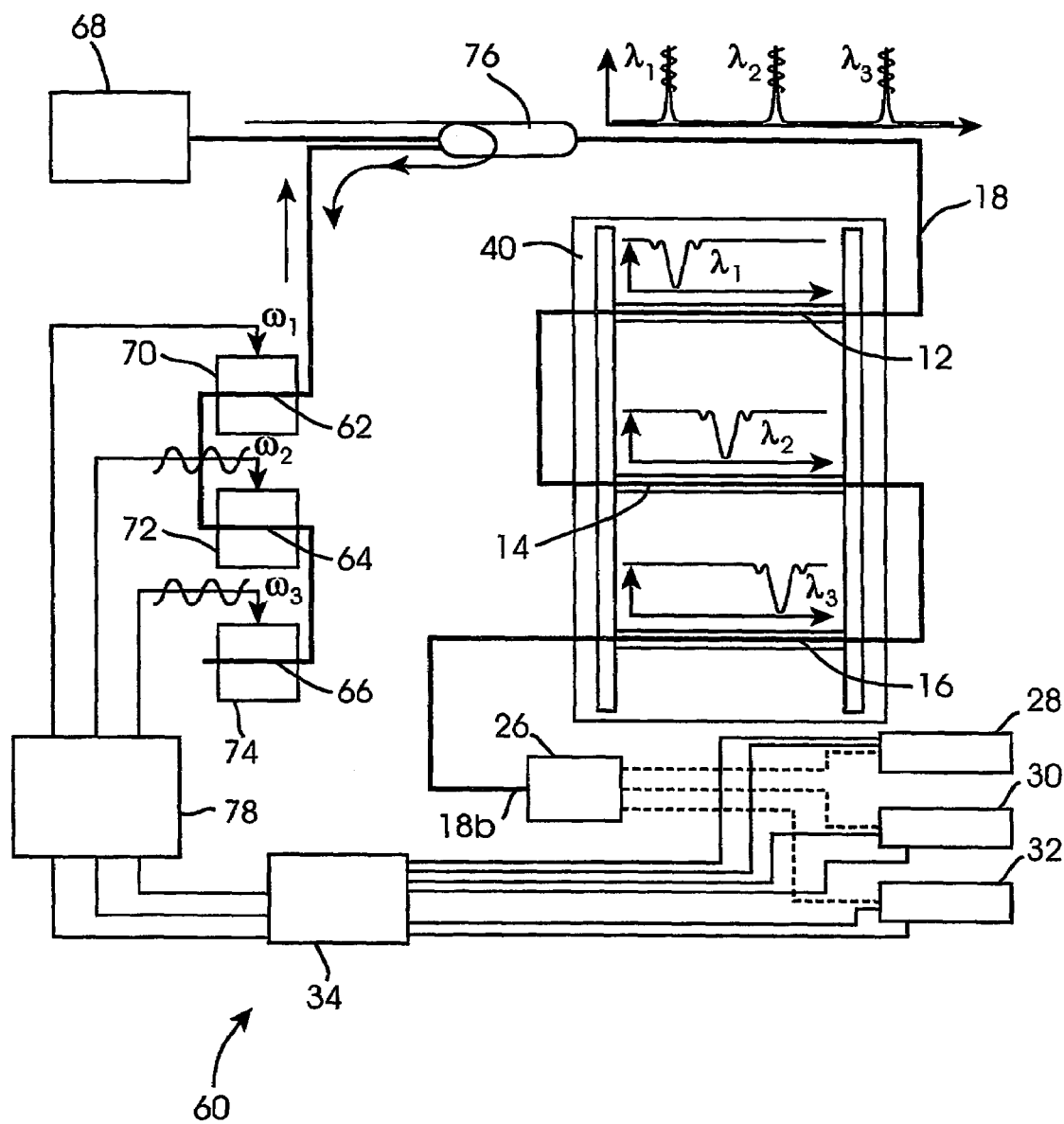
FIG. 10 is a schematic representation of surface profiling apparatus according to a second embodiment of the invention.

Surface profiling apparatus 60 according to a second embodiment of the invention is shown in FIG. 10. The apparatus 60 is substantially the same as the surface profiling apparatus 10 of the first embodiment, with the following modifications. The same reference numbers are retained for corresponding features.

In this embodiment the LPGs 12, 14, 16 are optically interrogated by wavelength modulated optical signals generated by illuminating three fibre Bragg gratings (FBGs) 62, 64, 66 with a broadband optical source in the form of a superluminescent light emitting diode (SLED) 68. The optical signal from the SLED 68 is routed to the FBGs 62, 64, 66 via an optical circulator (or coupler) 76. The light reflected by each of the FBGs 62, 64, 66 forms a narrow bandwidth optical signal which is coupled into the PTL fibre 18 through the circulator 76. Each optical signal has a central wavelength corresponding to the resonant wavelength of the respective FBG. Each FBG 62, 64, 66 has a different resonant wavelength, which lies within the spectral profile of its respective LPG 12, 14, 16. Each FBG 62, 64, 66 is coupled to tuning means in the form of a piezoelectric based strain apparatus 70, 72, 74 operable to apply an axial strain to the respective FBG 62, 64, 66 at a desired modulation frequency. A wavelength modulation at that modulation frequency is thereby applied to the resonant wavelength of the FBG 62, 64, 66.

Similarly to the first embodiment, the modulation signals at frequencies $\omega_1$, $\omega_2$ and $\omega_3$ are generated by a signal generator 34. The modulation signals are applied to the drive voltage supplied from a drive unit 78 to the piezoelectric element in each strain apparatus 70, 72, 74. The piezoelectric element in each strain apparatus is thereby caused to expand and contract at the desired modulation frequency, so applying a varying axial strain to the respective FBG 62, 64, 66. A different modulation frequency is applied to each FBG.

Figure 11:
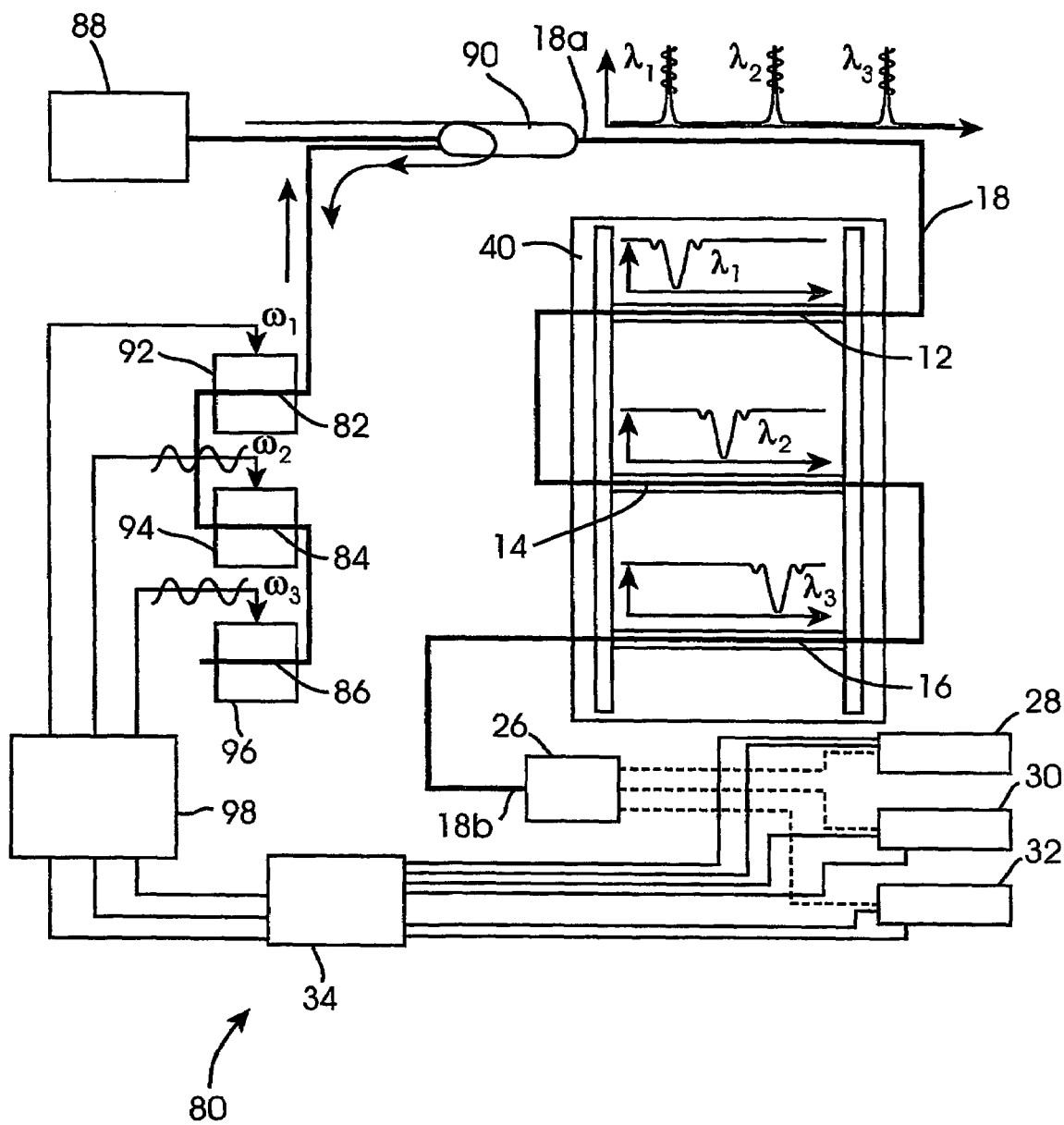
FIG. 11 is a schematic representation of surface profiling apparatus according to a third embodiment of the invention.

FIG. 11 shows surface profiling apparatus 80 according to a third embodiment of the invention. The apparatus 80 is substantially the same as the surface profiling apparatus 10 of the first embodiment, with the following modifications. The same reference numbers are retained for corresponding features.

In this embodiment the LPGs 12, 14, 16 are optically interrogated by wavelength modulated optical signals generated by three FBG fibre lasers 82, 84, 86. The laser cavity of each fibre laser 82, 84, 86 is formed by two FBGs provided in a spaced relationship in a section of erbium-doped single mode optical fibre; the FBGs and the fibre forming the laser cavity. The fibre lasers 82, 84, 86 are pumped by a 980 nm pump laser 88, optically coupled to the erbium-doped fibre via an optical circulator (or coupler) 90.

Each fibre laser 82, 84, 86 lases at a wavelength determined by the resonant wavelength of its FBGs. Each pair of FBGs have a different resonant wavelength to thereby give each fibre laser 82, 84, 86 a different operating wavelength. The optical output signal from each fibre laser 82, 84, 86 is coupled to the PTL fibre 18 via the circulator 90. Each pair of FBGs is coupled to tuning means in the form of a piezoelectric based strain apparatus 92, 94, 96 operable to apply an axial strain to the FBGs at a desired modulation frequency, to thereby apply a wavelength modulation at that modulation frequency to the resonant wavelength of the FBGs. When the resonant wavelength of the FBGs in a fibre laser 82, 84, 86 changes, the operating wavelength of the fibre laser also changes. Therefore, applying an axial strain to the FBGs of a particular fibre laser 82, 84, 86 at a desired modulation frequency will apply a wavelength modulation at that frequency to the output wavelength of the fibre laser 82, 84, 86. A different modulation frequency is applied to each fibre laser.

As in the first embodiment, the modulation signals at frequencies $\omega_1$, $\omega_2$ and $\omega_3$ are generated by a signal generator 34. The modulation signals are applied to the drive voltage supplied from a drive unit 98 to the piezoelectric element in each strain apparatus 92, 94, 96. The piezoelectric element in each strain apparatus is thereby caused to expand and contract at the desired modulation frequency, so applying a varying axial strain to the FBGs of the respective fibre laser 82, 84, 86.

Figure 12:
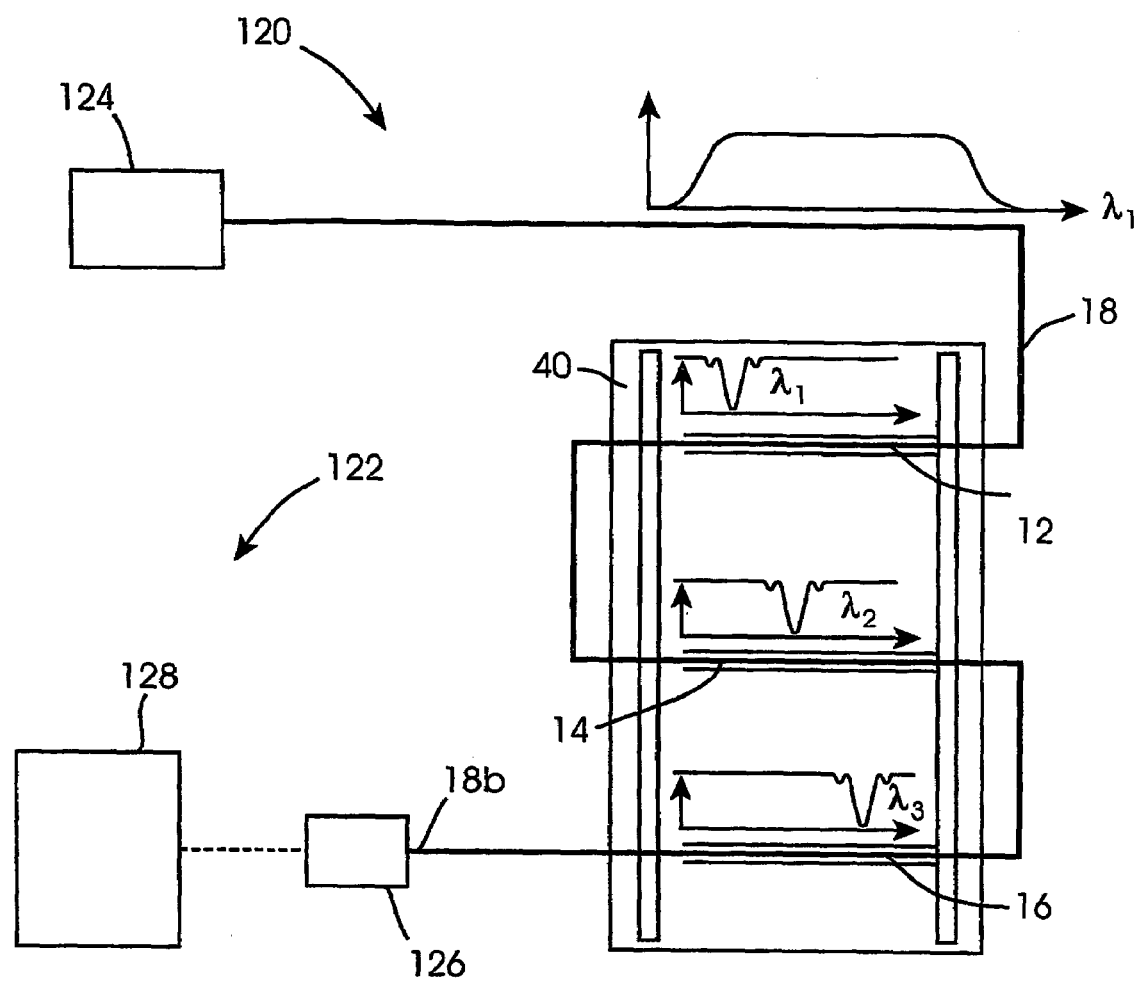
FIG. 12 is a schematic representation of surface profiling apparatus according to a fourth embodiment of the invention.

Surface profiling apparatus 120 according to a fourth embodiment of the invention is shown in FIG. 12. The apparatus 120 is similar to that shown in the first embodiment, but has different optical interrogation means 122, as described below. The same reference numbers are retained for corresponding features.

In this embodiment the LPGs 12, 14, 16 are illuminated by a broadband optical source in the form of a fibre pigtailed SLED 124, optically coupled to the input end 18a of the PTL fibre 18. The SLED 124 is operable to generate a broad bandwidth optical signal whose spectral range encompasses the spectral profiles of the attenuation bands of each of the LPGs 12, 14, 16. A small, portable optical spectrum analyser (OSA) 126, such as the "USB2000 Miniature Fiber Optic Spectrometer" from Oceanoptics Inc., is optically coupled to the output end 18b of the PTL fibre 18. The OSA 126 is operable to record the spectral profiles of the attenuation bands of each of the LPGs 12, 14, 16. The OSA 126 is connected to a microprocessor 128, which may be a personal computer, to which the recorded spectral profile data is downloaded. The microprocessor 128 is operable to compare the downloaded spectral profile data with a plurality of pre-recorded sets of spectral profile data, until a matching set of spectral profile data is found. Each set of pre-recorded spectral profile data corresponds to a particular curvature applied to a particular LPG, so a match indicates the curvature experienced by the LPG 12, 14, 16 under interrogation. The OSA 126 may be permanently connected to the microprocessor 128, so that each recorded set of spectral profile data can be downloaded to, and processed by, the microprocessor 128 in real time. Alternatively, the OSA 126 does not have to be connected to the microprocessor 128 during interrogation of one or more LPGs 12, 14, 16. A number of spectral profiles may be recorded and stored in the OSA 126 for later downloading to, and processing by, the microprocessor 128 once the OSA 126 is connected to it.

Figure 13:
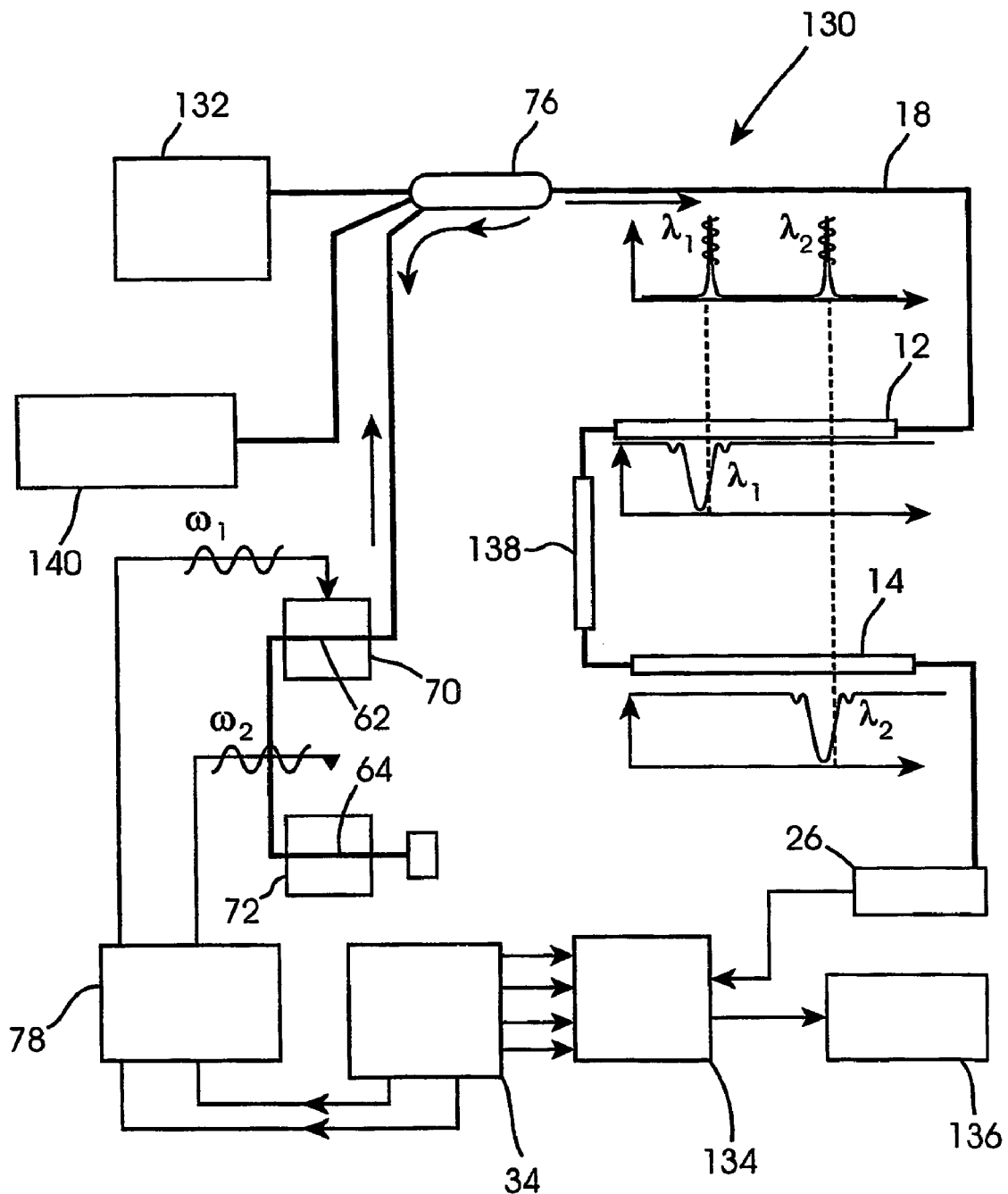
FIG. 13 is a schematic representation of surface profiling apparatus according to a fifth embodiment of the invention.

FIG. 13 shows surface profiling apparatus 130 according to a fifth embodiment of the invention. The apparatus 130 is substantially the same as the surface profiling apparatus 10 of the first embodiment, with the following modifications. The same reference numbers are retained for corresponding features.

In this embodiment only two LPGs 12, 14 are provided within the PTL fibre 18. The skilled person will however appreciate that a larger number of LPGs may be provided. As a result, only two wavelength modulated optical signals are required to interrogate the LPGs 12, 14. The interrogating optical signals are generated by illuminating two fibre Bragg gratings (FBGs) 62, 64 with a broadband optical source, which in this example takes the form of the spontaneous emission generated by an Erbium doped fibre amplifier (EDFA) 132. As in the first embodiment, the optical signal from the EDFA 132 is routed to the FBGs 62, 64 via an optical circulator (or coupler) 76. The light reflected by each of the FBGs 62, 64, 66 forming a narrow bandwidth optical signal which is coupled into the PTL fibre 18 through the circulator 76. Each FBG 62, 64 is coupled to tuning means in the form of a piezoelectric based strain apparatus 70, 72 operable to apply an axial strain to the respective FBG 62, 64 at a desired modulation frequency. A wavelength modulation at that modulation frequency is thereby applied to the resonant wavelength of the FBG 62, 64.

In this example, the electrical output of the photodetector 26 is connected to a single lock-in amplifier 134, operable at multiple frequencies. The output from the lock-in amplifier 134 is passed to a data processing and storage device 136.

The curvature sensors, LPGs 12, 14, detect any variations in the shape of the surface under interrogation. In some instances, when the surface under interrogation is expandable, for example a human torso, the positions of the LPGs 12, 14 relative to one another must also be monitored, in order to take into account variations in the volume enclosed within the surface. This is achieved here by providing an optical waveguide strain sensor, in the form of an fibre Bragg grating (FBG) 138, at a location between the LPGs 12, 14. The FBG 138 measures the strain in the section of PTL fibre 18 between the LPGs 12, 14, from which variations in the distance separating the two LPGs 12, 14 can be determined.

The skilled person will appreciate that where more than two LPGs are provided, an FBG strain sensor may be provided between each pair of LPGs. The FBG 138 or FBGs may alternatively be provided generally alongside, and substantially parallel to, an LPG 12, 14. The FBG 138 or FBGs would generally be provided within a separate optical fibre (not shown), which may be standard single mode fibre.

In this embodiment the optical interrogation means further comprises means 140 for interrogating the FBG 138 strain sensor in reflection. The FBG interrogation means 140 may comprise any of the know systems for interrogating FBGs, which will be well known to the person skilled in the art and so will not be described in detail here. The FBG interrogation means 140 may alternatively take the form of an optical waveguide grating interrogation system according to our co-pending European patent application number 02258640.8.

Figure 14:
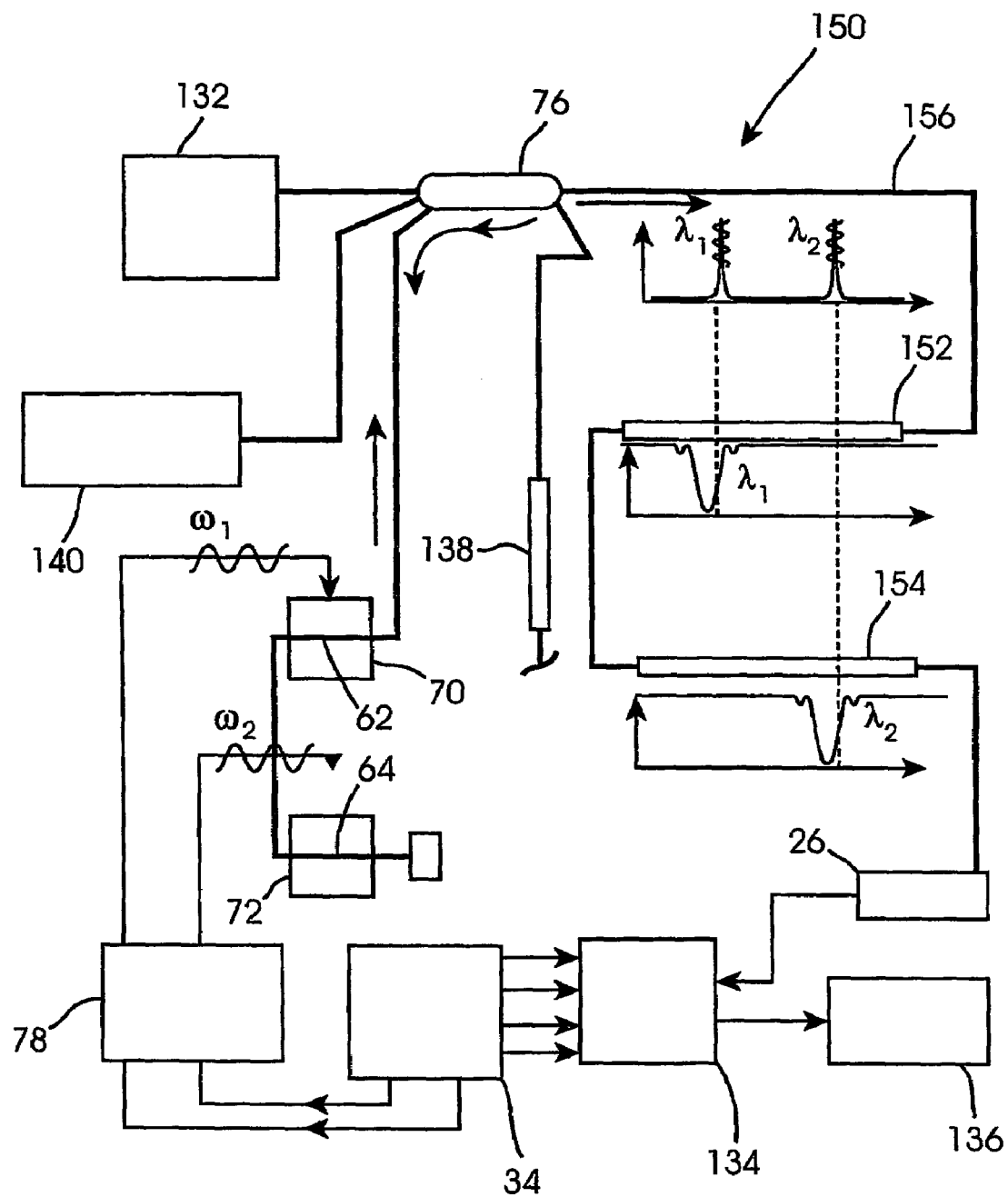
FIG. 14 is a schematic representation of surface profiling apparatus according to a sixth embodiment of the invention.

Surface profiling apparatus 150 according to a sixth embodiment of the invention is shown in FIG. 14. The apparatus 150 according to this embodiment is substantially the same as the apparatus 130 of the previous embodiment with the following modifications. The same reference numerals are retained for corresponding features.

In this embodiment the optical waveguide grating curvature sensing devices take the form of chirped FBGs 152, 154. Although only two FBGs 152, 154 are shown, the skilled person will again appreciate that a larger number of FBG curvature sensors may be provided. The response, i.e. the change in the spectral profile, of the FBGs 152, 154 to curvature/bending may be further or alternatively enhanced by fabricating the FBGs 152, 154 such that the amplitude of the periodic refractive index variation of the Bragg grating is tapered and/or apodised.

The FBGs 152, 154 are provided within an asymmetric optical fibre having a radially asymmetric cladding layer, which in this example takes the form of D-shaped fibre 156.

In this embodiment the FBG strain sensor 138 is provided in a separate optical waveguide, which takes the form of a standard single mode optical fibre 158.

Figure 15:
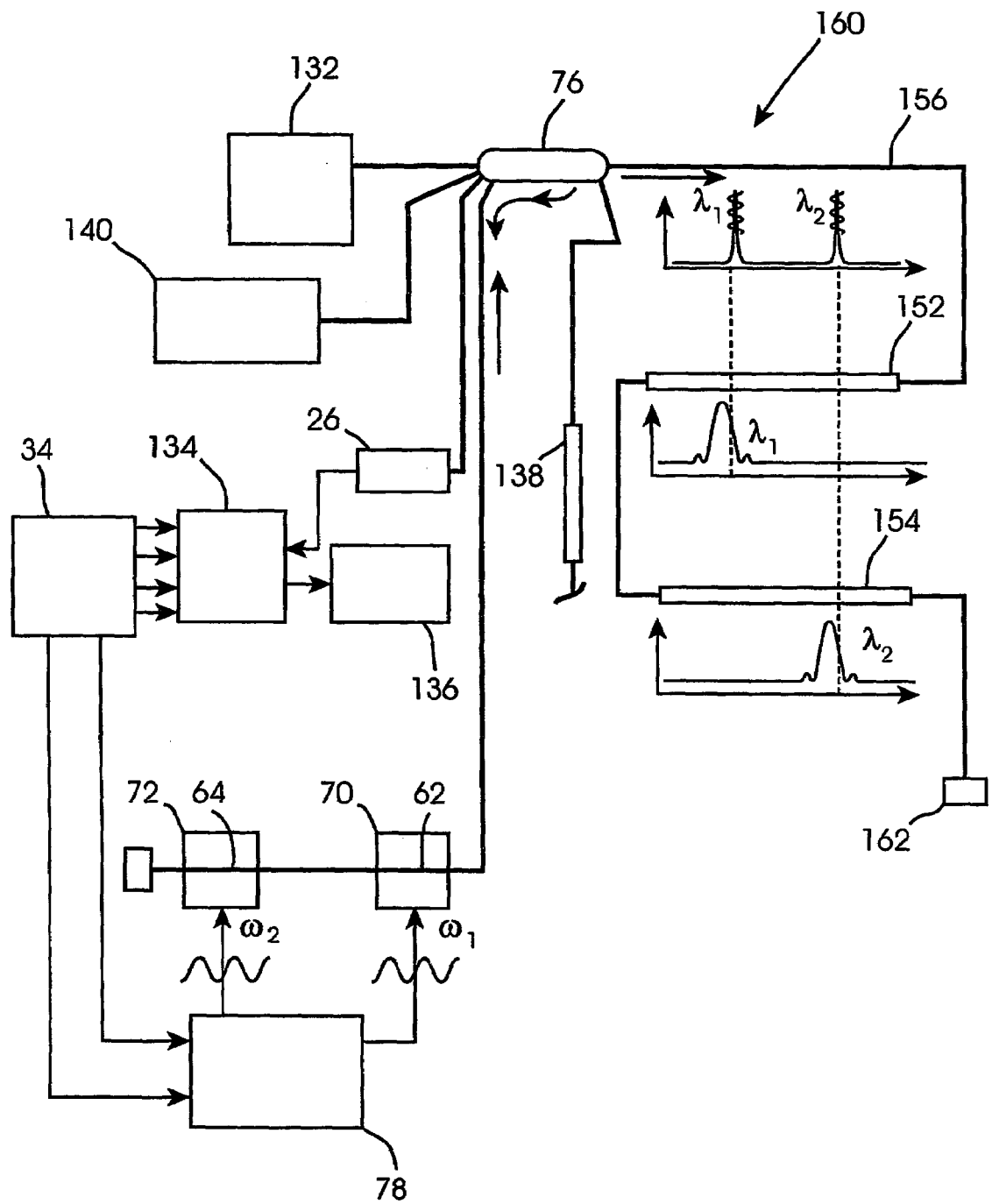
FIG. 15 is a schematic representation of surface profiling apparatus according to a seventh embodiment of the invention.

FIG. 15 shows surface profiling apparatus 160 according to a seventh embodiment of the invention. The apparatus 160 is substantially the same as the apparatus 150 of the previous embodiment, with the following modifications. The same reference numerals are retained for corresponding features.

In this embodiment the FBG curvature sensors 152, 154 are interrogated in reflection. Therefore, instead of the photodetector 26 being located at the distal end of the optical fibre 156, the photodetector is coupled to a port of the optical circulator 76. The distal end of the fibre 156 is terminated in an optical dump 162.

Referring to FIGS. 16 to 20, an eighth embodiment of the invention provides respiratory function monitoring apparatus 100 comprising surface profiling apparatus 102 which is substantially the same as the surface profiling apparatus 10, 60, 80, 120 according to one of the first, second, third or fourth embodiments, with the following modifications. The same reference numbers as in the first embodiment are used for corresponding features (the first embodiment is selected for illustration only, and the skilled person will understand that the surface profiling apparatus according to any of the second to seventh embodiments may be used instead).

Figure 16:
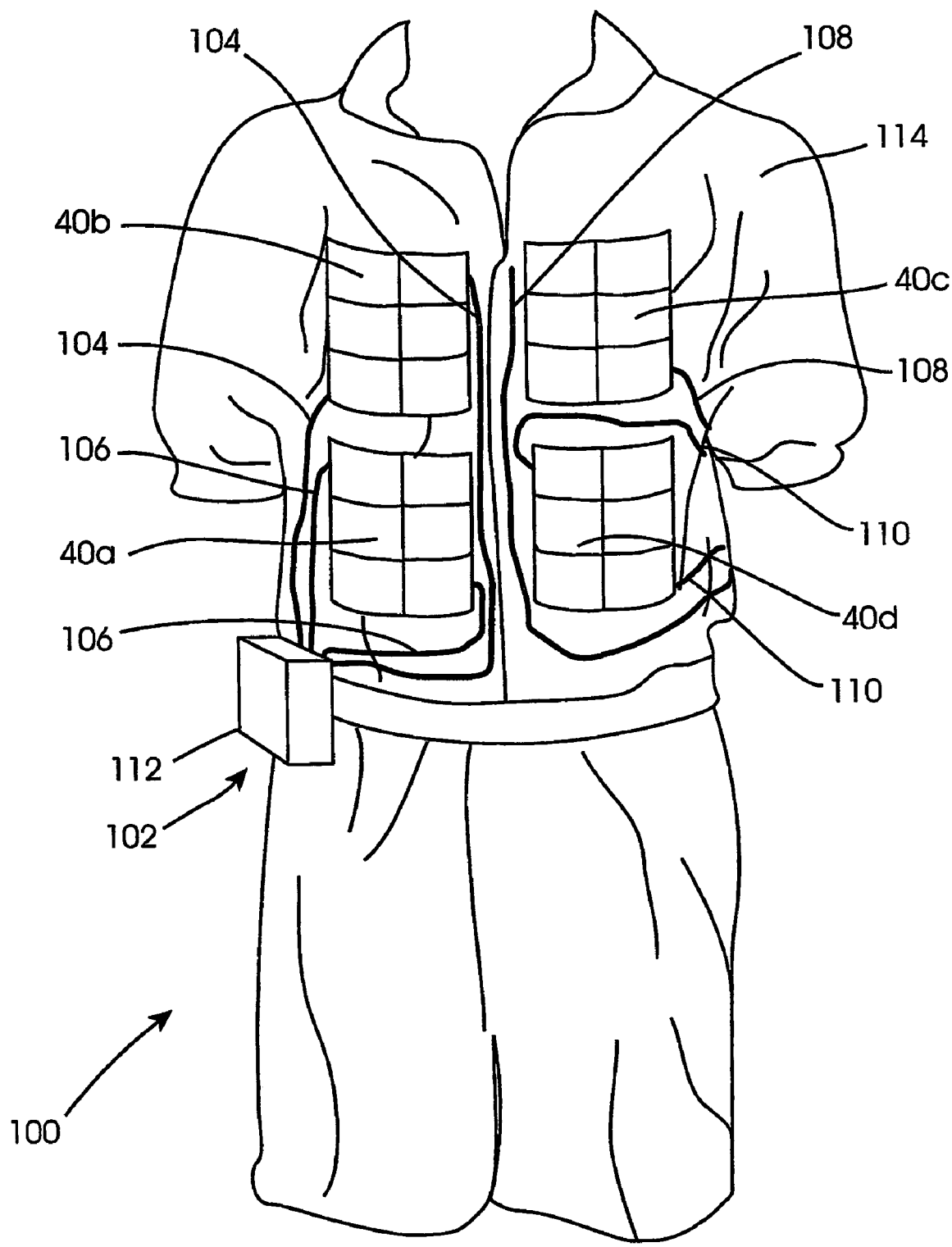
FIG. 16 is a diagrammatic representation of respiratory function monitoring apparatus according to a eighth embodiment of the invention.

As shown in FIG. 16, in this example five LPGs (not shown) are provided within each of four carrier members 40a–d, giving a total of 20 LPGs. Each set of five LPGs are provided within a different PTL fibre 104, 106, 108, 110. There are four different optical arrangements which may be used to deal with this large number of LPGs. In the first, the attenuation band of each LPG has a different central wavelength and the LPGs are interrogated by twenty wavelength modulated, narrow bandwidth optical signals generated by twenty DBF lasers (as in the first embodiment shown in FIG. 1), by an SLED and twenty FBGs (as in the second embodiment shown in FIG. 10), or by twenty fibre lasers (as in the third embodiment shown in FIG. 11). The wavelength of each optical signal is different, lying within the spectral bandwidth of the respective LPG, and each optical signal is wavelength modulated at a different modulation frequency. The output end of each PTL fibre 104, 106, 108, 110 is coupled to a single photodetector 26, and the electrical output signal from the photodetector is connected to twenty lock-in amplifiers, each operating at the first and second harmonics of the modulation frequency of their respective optical signals.

In the second optical arrangement the attenuation band of each LPG again has a different central wavelength. The twenty LPGs are illuminated by a single broadband optical source, for example an SLED or an edge-emitting light emitting diode (EELED). The spectral profiles of the attenuation bands are recorded by a single OSA and compared to pre-recorded spectral profiles using a microprocessor (as in the fourth embodiment shown in FIG. 12).

In the third optical arrangement, each LPG within a set of five LPGs has a different attenuation band central wavelength, the LPGs in each of the four sets having the same five central wavelengths. This means that only five narrow bandwidth optical signals, having five different wavelengths, are required to interrogate all twenty LPGs, since each optical signal can be used to interrogate four separate LPGs. By connecting the output end of each PTL fibre 104, 106, 108, 110 to a different photodetector, only five different wavelength modulation frequencies are required. The photodetectors thereby identify which carrier member 40a–d a signal relates to, and the modulation frequency identifies the LPG within that carrier member 40a–d, thereby identifying the respective monitoring location.

The fourth optical arrangement similarly uses four sets of five LPGs. In this case all of the LPGs can be illuminated using a single broadband optical source, SLED or EELED. The output end of each PTL fibre 104, 106, 108, 110 is connected to a different OSA, since the LPGs within each set are identified by wavelength. The spectral profiles recorded by the OSAs can be downloaded to a single microprocessor for processing to determine the curvature experience by each LPG, as in the fourth embodiment.

In this embodiment the respiratory function monitoring apparatus 100 is intended for use on a human subject and the curvature values are used to generate a 3-dimensional wireframe image of the thoracoabdominal surface. Testing of the apparatus 100 was carried out on a commercial resuscitation training aid manikin. The manikin comprises a rigid underframe over which a polymer skin is stretched. An inflatable air bag is provided between the frame and skin, and can be inflated and deflated to simulate expansion and contraction of the surface of the torso in similar volumetric proportions to that of breathing.

The number of LPGs required to monitor the respiratory function of an adult human subject was determined using chest profile data obtained from a CT imager. The upper chest geometry of a male subject was reconstructed using a $7^{th}$ order polynomial and the surface area evaluated. This was then compared to the area estimated using simple trapezoidal and four-point cubic-spline integrations at lower sampling resolutions in order to obtain an estimate of the error dependence on the number of monitoring locations, i.e. the number of LPGs, within the surface profiling apparatus 102.

Figure 17:
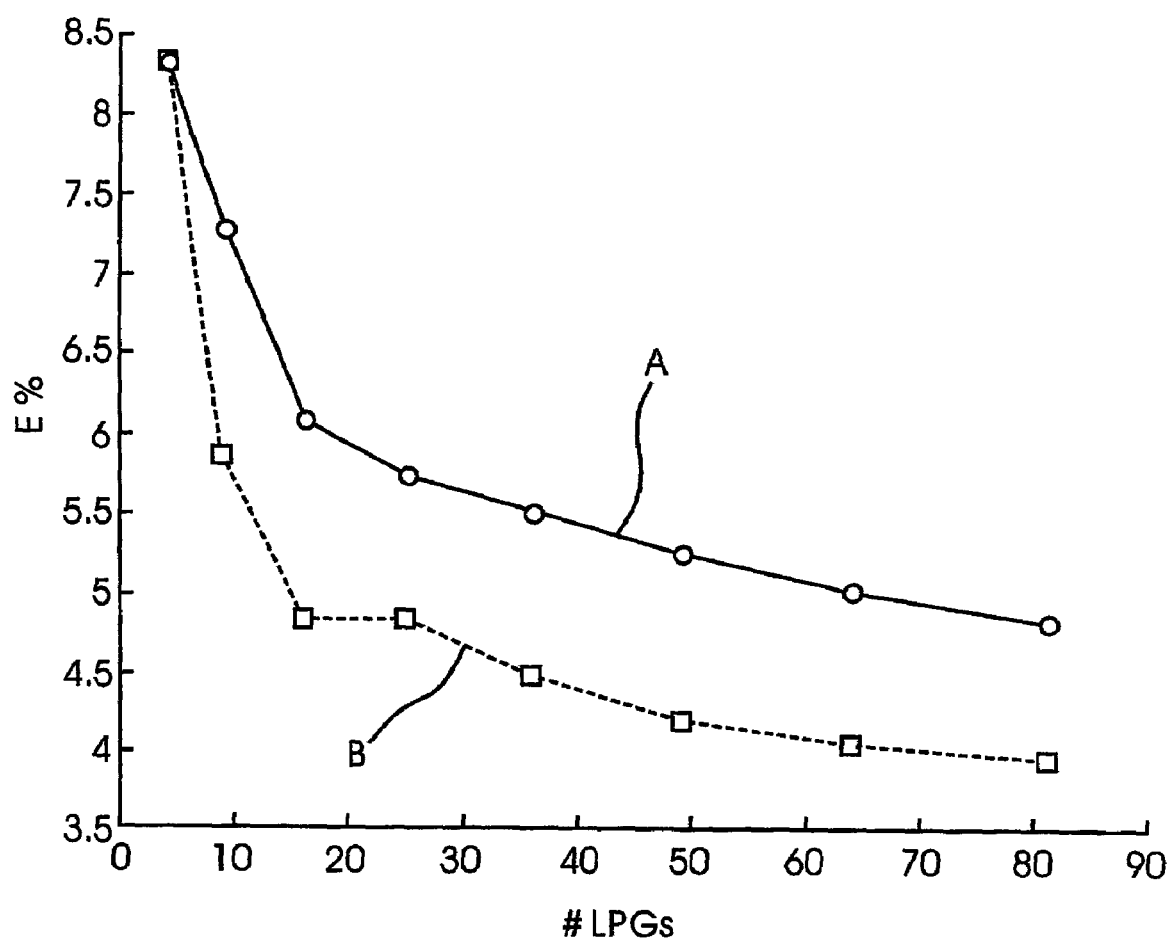
FIG. 17 shows plots of percentage surface area error (E) as a function of number of monitoring locations for reconstructed CT scan chest profile data: (A) trapezoidal approximation; and (B) 4-point cubic spline interpolation.

FIG. 17 shows a plot (A) of surface area error (calculated using the trapezoidal integration) as a function of the number of monitoring locations/LPGs provided across a torso (assuming that the same resolution is required longitudinally and laterally). The second plot (B) shows surface area error (calculated using the cubic-spline interpolation) as a function of number of LPGs. Considering these values together with generally accepted volumetric performance standards for spirometry function respiratory function monitoring devices, confirms that the respiratory function monitoring apparatus 100 requires in the region of 20 LPGs (using cubic-spline interpolation) to provide a similar performance.

The response LPG within one carrier member 40 was investigated, using an OSA, at various degrees of inflation of the manikin, at five different locations on the manikin. Each location is represented by a set of dimensions given in the following table, and shown in FIG. 18.

Figure 18:
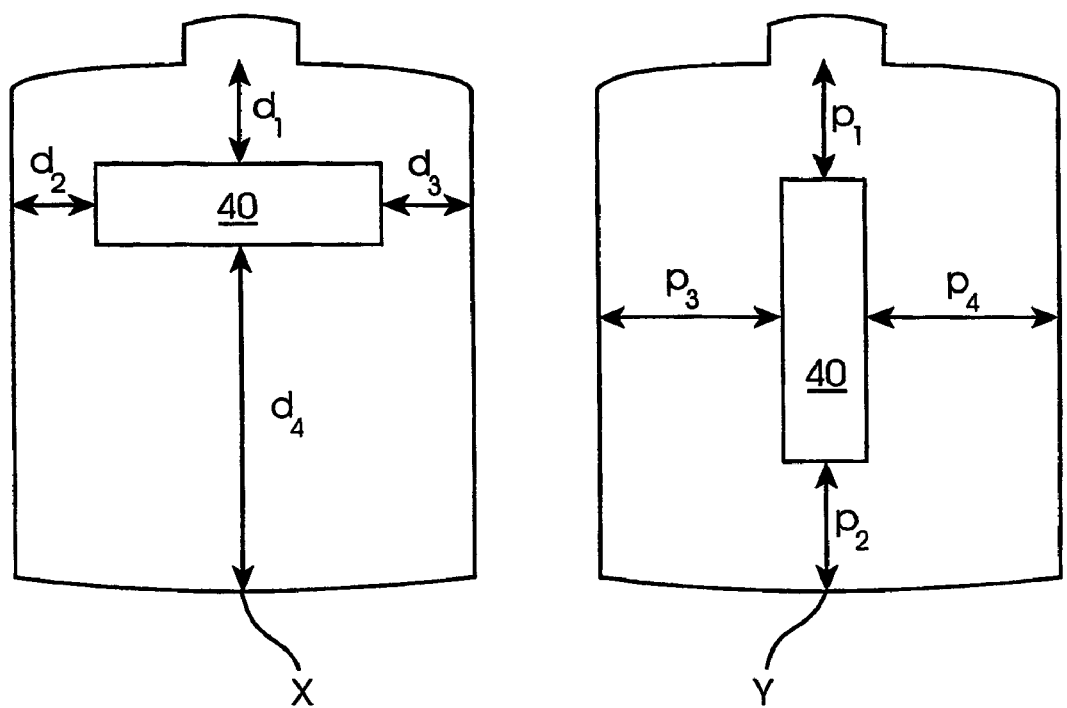
FIG. 18 is a diagrammatic representation of a torso showing the location of the carrier member on the upper chest (X) and the lower chest (Y)

| Position on torso FIG. 18 (X) | $d_1$ (mm) | $d_2$ (mm) | $d_3$ (mm) | $d_4$ (mm) | Maximum detected wavelength shift (nm) |
|---|---|---|---|---|---|
| 1 | 90 | 50 | 50 | 250 | 1.05 |
| 2 | 185 | 50 | 50 | 185 | 3.18 |
| 3 | 287 | 50 | 50 | 75 | 0.95 |
| Position on torso FIG. 18 (Y) | $p_1$ (mm) | $p_2$ (mm) | $p_3$ (mm) | $p_4$ (mm) | Maximum detected wavelength shift (nm) |
| 4 | 205 | 25 | 165 | 165 | 1.98 |
| 5 | 100 | 128 | 165 | 165 | 1.70 |

The change in the central wavelength of the LPG's attenuation band as a function of the peripheral expansion of the manikin's skin (change in the circumference of the manikin's torso) was also investigated, shown in FIGS. 19 and 20. The variation in response of the LPG apparent between locations on the upper and lower chest regions mimics that which might be expected in a real human subject, as the expansion of the rib cage has a more significant contribution at higher levels of ventilation.

FIGS. 19 and 20 show that the spectral response of the LPG as a function of peripheral expansion of the manikin's skin varies with location on the torso. The errors shown in these figures correspond to the spectral accuracy (±0.04 nm) of the OSA used to measure the change in wavelength and a torso circumference error of ±1 cm. The circumference error is an estimate of the variation of the manikin's skin deformation between each set of results.

As discussed above in connection with the first embodiment, LPGs are temperature sensitive, although this has been reduced by an order of magnitude due to the fact that the LPGs 12, 14, 16 are fixed to steel support strips 50, 52, 54. The temperature sensitivity of the LPGs will introduce an error into the measurement process during monitoring of respiratory function, since the surface profiling apparatus 10, 60, 80 is intended to be used in close contact with the skin. Assuming a typical skin temperature variation of ~32° C. to ~35° C. this would generate a maximum wavelength error of ±0.035 nm. Using the maximum detected wavelength shift presented in the above table, this gives a maximum (worst case) relative error of ~±3% (position 3) and a minimum relative error of ~±1% (position 2).

As shown in FIG. 16 the carrier members 40a–d are attached to a garment 114 which is worn by the subject. The garment 114 shown is illustrative only and would in practice be of a closer fit to the subject's skin, so that the carrier members 40a–d are in close contact with the skin. Providing the carrier members 40a–d on a garment 114 assists in the correct positioning of the LPGs across the surface to be profiled, i.e. the torso. The optical interrogation means 112 in this example is carried by a belt 116 worn around the subject's waist, but it could alternatively be attached to the garment 114, or be provided with attachment means, such as a mechanical clip or fleece and hook fastener, by which the subject may attach the optical interrogation means 112 to an item of clothing.

The surface profiling apparatus of the described embodiments provide the advantage of having a curvature spectral sensitivity of 3.747 nm.m and the temperature sensitivity of the LPGs is reduced by approximately an order of magnitude by mounting them on carbon steel support strips. The LPGs display negligible axial strain due to their being fixed to the support strips. The surface profiling apparatus can be used to distinguish between various geometric variations associated with different locations on a moving surface, including a human torso during respiratory movement. The fabrication of the LPGs in a multi-clad single mode optical fibre, such as PTL, makes the LPGs insensitive to the refractive index of a surrounding medium. Each of the described optical interrogation apparatus is portable, enabling the profile of a surface to be monitored in a real situation (i.e. outside of a laboratory environment) and allows the subject on which the surface is located to move freely during measurement and monitoring.

The surface profiling apparatus does not need to be calibrated for each surface under investigation. The optical grating sensors (LPGs) only need to be calibrated once: change in the electrical output signal as a function of change in curvature experienced by an LPG.

The respiratory function monitoring apparatus described provides monitoring apparatus which can assess lung function without the need for flow measurement at the mouth. The apparatus can also provide detailed information of the dynamics of chest motion during breathing. The described apparatus will facilitate further studies of respiratory physiology, because unlike previously known systems, it can provide a completely non-invasive and quantitative appreciation of respiratory function. Using 20 LPG sensors allows the apparatus to be used to generate a geometrical profile of the chest and abdomen in three dimensions with the necessary accuracy. The apparatus provides a curvature resolution of $\pm 2.0 \times 10^{-2}$ m$^{-1}$ which is a relative error of $\pm 1\%$ over the curvature measurement range of the apparatus.

The respiratory function monitoring apparatus described re-approaches the less complex, useful two compartment monitoring technology from a geometrical aspect with a view to enhancing the performance and adding functionality. The apparatus enables a 3-dimensional profile of the thoracoabdominal surface to be generated, using an on-body reference. The apparatus enables the movement of selected anatomical positions on the chest and abdomen surface to be tracked during breathing manoeuvres, as well as facilitating measurements of tidal respiratory volume. The curvature values generated by the apparatus are input into a surface-modelling algorithm to create a 2- or 3-dimensional wire-frame image of the thoracoabdominal surface.

The electronic and optical elements of the optical interrogation means can be made very small and therefore portable. This means that the respiratory function monitoring apparatus can be attached to the subject, enabling the subject to move freely without constraint whilst their breathing is monitored. The apparatus thereby provides an improved diagnostic tool for continuous monitoring of patients in a healthcare environment.

Various modifications may be made without departing from the scope of the invention. Referring to the surface profiling apparatus itself, a different type of optical fibre may be used to that described, including multilayer optical fibres having three or more cladding layers. The structure of the optical fibre may be asymmetrical about its axis. The LPGs may include sections in which the grating period is chirped, or may include one or more phase-shifts within the periodic refractive index modulation, to provide additional information about the direction of the curvature. The LPGs may alternatively or additionally be asymmetric about the axis of the fibre. The LPGs may be replaced by an alternative optical waveguide grating curvature sensing device, such as two long period gratings arranged to together define an in-line Mach-Zehnder interferometer, an optical waveguide Bragg grating, or two optical waveguide Bragg gratings arranged to together define a Fabry-Perot etalon.

The coupling means may comprise a different number of carrier members to that described, and a different number of optical waveguide grating curvature sensing devices may by provided within each carrier member. In particular, a single carrier member, of a size and shape suitable to provide a close fit to the surface to be profiled, may be used. The arrangement of the LPGs within a carrier member may be different to that used. The carrier member may have a different structure to that described, in particular a skeleton may not be necessary for mechanically strong types of optical fibre, such as polymer fibre. The skin of the carrier member may comprise a different flexible material.

In the case of an inanimate subject a carrier member may not be required, the optical waveguide grating curvature sensing devices being attached directly to, or embedded within, the surface to be profiled.

The optical interrogation means may utilise different optical sources operable to generate a wavelength modulated, narrow bandwidth optical signal. Also, different optical detection means may be used to that described. In particular, a different number of photodetectors may be used and the lock-in amplifiers may be replaced by a different type of synchronous detector. A different optical spectrum analyser to that described by be used in connection with the surface profiling apparatus of the described fourth embodiment.

Referring in particular to the respiratory function monitoring apparatus, a different number of carrier members may be used, and each carrier member may incorporate a different number of LPGs. The garment incorporating the carrier members may be different to that described.

The inventon claimed is:

1. A surface profiling apparatus (10, 60, 80, 102, 120) comprising:
   an optical waveguide including a plurality of sensor sections, each sensor section comprising a respective optical waveguide grating curvature sensing device, each optical waveguide grating curvature sensing device comprising at least one long period grating (12, 14, 16); and
   optical interrogation means operable to interrogate the optical waveguide grating curvature sensing devices to determine the curvature experienced by each device, the optical interrogation means comprising:
      an optical source optically coupled to one, input, end (18a) of the respective optical waveguide and being operable to generate a narrow spectral bandwidth optical signal at a wavelength within the spectral range of an optical waveguide grating curvature sensing device to be interrogated, the optical signal being wavelength-modulated at a modulation frequency; and
      optical detection means optically coupled to the other, output, end (18b) of the optical waveguide and being operable to measure the amplitude of a detected optical signal at least one harmonic of the modulation frequency in order to detect changes in the spectral transmission profile of the optical waveguide grating curvature sensing device being interrogated and to thereby determine the curvature experienced by the optical waveguide grating curvature sensing device;
   whereby the sensor sections are couplable to a surface to be profiled, and a profile of said surface is constructed from the curvatures sensed by the optical waveguide grating curvature sensing devices.

2. The apparatus of claim 1, wherein the optical waveguide is an optical fibre (18) such as a silica-glass optical fibre or a polymer optical fibre, the optical fibre (18) comprising a core, an inner cladding layer surrounding the core, and at least a first outer cladding layer surrounding the inner cladding layer, the refractive index of the inner cladding layer being less than the refractive index of the core, and the refractive index of the first outer cladding layer being less than the refractive index of the inner cladding layer.

3. The apparatus of claim 2, wherein the optical fibre (18) further comprises a second outer cladding layer surrounding the first outer cladding layer in order to isolate light propagating within a cladding mode of the inner cladding layer from a medium surrounding the second outer cladding layer, the refractive index of the second outer cladding layer being less than the refractive index of the first outer cladding layer.

4. The apparatus of claim 1, wherein the at least one long period grating (12, 14, 16) comprises two long period gratings arranged to together define an in-line Mach-Zehnder interferometer.

5. The apparatus of claim 1, further comprising coupling means for coupling the sensor sections to the surface to be profiled, the coupling means comprising a carrier member (40), and the sensor sections of the optical waveguide being fixed to or embedded within the carrier member (40).

6. The apparatus of claim 5, wherein the coupling means comprises a plurality of carrier members (40) mounted on a support structure, one or more sensor sections being fixed to or embedded within each carrier member (40).

7. The apparatus of claim 6, wherein each carrier member (40) is deforniable and comprises a flexible skin fixed to a partially rigid, expandable skeleton structure.

8. The apparatus of claim 5, wherein the carrier member (40) is deformable and comprises a flexible skin fixed to a partially rigid, expandable skeleton structure.

9. The apparatus of claim 5, further comprising a respiratory function monitoring apparatus (100) operable to utilize the surface profiling apparatus (10,60, 80, 102, 120) for use on the rib cage or torso during respiratory movement.

10. The apparatus of claim 1, wherein the optical interrogation means is at least one of a derivative spectroscopy and a synthetic heterodyne based optical interrogation means operable to detect changes in the spectral profile of an optical waveguide grating curvature sensing device.

11. The apparatus of claim 10, wherein the optical detection means comprises:

a photodetector (26) optically coupled to the output end (18*b*) of the or each optical waveguide and a plurality, corresponding to the number of optical waveguide grating curvature sensing devices provided within the respective waveguide, of lock-in amplifiers (28, 30, 32) or synchronous detectors each operable to measure the amplitude of a detected optical signal at the modulation frequency associated with a particular optical waveguide grating curvature sensing device and a harmonic of the modulation frequency; and data processing means connected to the photodetector (26), operable to calculate the ratio of the amplitudes and the arc tangent of the ratio of the amplitudes, to which the curvature experienced by the optical waveguide grating curvature sensing device under interrogation is linearly related.

* * * * *